US012637465B2

(12) United States Patent
Levy et al.

(10) Patent No.: US 12,637,465 B2
(45) **Date of Patent: *May 26, 2026**

(54) PHARMACEUTICALLY ACCEPTABLE SALTS OF SEPIAPTERIN

(71) Applicant: PTC Therapeutics MP, Inc., South Plainfield, NJ (US)

(72) Inventors: Daniel E. Levy, San Mateo, CA (US); Neil Smith, Cary, NC (US); Jonathan Reis, Brookline, MA (US); Hiroshi Yoshino, Narashino (JP); Taichi Komoda, Narashino (JP); Yuichi Shiro, Narashino (JP); Shunichi Murata, Narashino (JP); Takayoshi Matsumoto, Narashino (JP); Kaito Kishimoto, Narashino (JP)

(73) Assignee: PTC Therapeutics MP, Inc., Warren, NJ (US)

( * ) Notice: Subject to any disclaimer, the term of this patent is extended or adjusted under 35 U.S.C. 154(b) by 1106 days.

This patent is subject to a terminal disclaimer.

(21) Appl. No.: 17/059,887

(22) PCT Filed: May 30, 2019

(86) PCT No.: PCT/US2019/034505

§ 371 (c)(1),
(2) Date: Nov. 30, 2020

(87) PCT Pub. No.: WO2019/232120

PCT Pub. Date: Dec. 5, 2019

(65) Prior Publication Data

US 2021/0269443 A1 Sep. 2, 2021

Related U.S. Application Data

(60) Provisional application No. 62/822,336, filed on Mar. 22, 2019, provisional application No. 62/726,612, filed on Sep. 4, 2018, provisional application No. 62/678,025, filed on May 30, 2018.

(30) Foreign Application Priority Data

May 28, 2019 (GC) ................................ 2019/37661

(51) Int. Cl.
*C07D 475/04* (2006.01)
*A61K 45/06* (2006.01)

(52) U.S. Cl.
CPC ............ *C07D 475/04* (2013.01); *A61K 45/06* (2013.01); *C07B 2200/13* (2013.01)

(58) Field of Classification Search
CPC .... C07D 475/04; C07D 213/80; A61K 45/06; A61K 31/519; C07B 2200/13; C07C 55/08; C07C 57/15; C07C 59/06; C07C 65/05; C07C 309/04; C07C 309/29; C07C 209/04; C07C 209/30; A61P 25/00
See application file for complete search history.

(56) References Cited

U.S. PATENT DOCUMENTS

| | | | | |
|---|---|---|---|---|
| 4,758,571 | A | 7/1988 | Curtius et al. | |
| 4,774,244 | A | 9/1988 | Curtius et al. | |
| 5,736,343 | A | 4/1998 | Landry | |
| 5,753,656 | A * | 5/1998 | Sakai .................. | C07D 475/04 514/249 |
| 7,566,462 | B2 | 7/2009 | Jungles et al. | |
| 7,566,714 | B2 | 7/2009 | Oppenheimer et al. | |
| 7,582,799 | B2 | 9/2009 | Yoshino et al. | |
| 7,612,073 | B2 | 11/2009 | Oppenheimer et al. | |
| 7,727,987 | B2 | 6/2010 | Moser et al. | |
| 7,732,599 | B2 | 6/2010 | Moser et al. | |
| 7,947,681 | B2 | 5/2011 | Oppenheimer et al. | |
| 8,003,126 | B2 | 8/2011 | Jungles et al. | |
| 8,067,416 | B2 | 11/2011 | Oppenheimer et al. | |
| 8,188,043 | B2 | 5/2012 | Cooke et al. | |
| 8,222,422 | B2 | 7/2012 | Hashimoto et al. | |
| RE43,797 | E | 11/2012 | Oppenheimer et al. | |
| 8,318,745 | B2 | 11/2012 | Moser et al. | |
| 8,410,264 | B2 | 4/2013 | Dai et al. | |
| 9,181,254 | B2 | 11/2015 | Yoshino et al. | |
| 9,212,183 | B2 | 12/2015 | Sieger et al. | |
| 9,433,624 | B2 | 9/2016 | Oppenheimer et al. | |
| 9,492,451 | B2 | 11/2016 | Rustomjee et al. | |

(Continued)

FOREIGN PATENT DOCUMENTS

| | | |
|---|---|---|
| JP | 2020-532535 A | 11/2020 |
| MX | 2019/006206 A | 8/2019 |

(Continued)

OTHER PUBLICATIONS

U.S. Appl. No. 17/059,632, PTC Therapeutics MP, Inc.
U.S. Appl. No. 17/059,719, PTC Therapeutics MP, Inc.
Bernegger et al., "High frequency of tetrahydrobiopterin-responsiveness among hyperphenylalaninemias: a study of 1,919 patients observed from 1988 to 2002," Mol Genet Metab. 77(4): 304-13 (2002).
Blau et al., "Tetrahydrobiopterin deficiencies without hyperphenylalaninemia: diagnosis and genetics of DOPA-responsive dystonia and sepiapterin reductase deficiency," Mol Genet Metab. 74(1-2): 172-85 (2001).

(Continued)

*Primary Examiner* — Rayna Rodriguez
(74) *Attorney, Agent, or Firm* — Clark & Elbing LLP

(57) ABSTRACT

The present invention relates to new pharmaceutical salts and/or co-crystals of sepiapterin which exhibit improved properties. In particular, the invention relates to salts of sepiapterin with improved stability. The invention also relates to pharmaceutical compositions including a pharmaceutically effective amount of one or more salts and/or co-crystals of sepiapterin, as well as methods of treating tetrahydrobiopterin-related disorders including administration of a sepiapterin salt and/or co-crystal of the invention to a subject in need thereof.

8 Claims, 13 Drawing Sheets

(56) References Cited

U.S. PATENT DOCUMENTS

| | | | |
|---|---|---|---|
| 9,993,481 | B2 | 6/2018 | Oppenheimer et al. |
| 11,072,614 | B2 | 7/2021 | Levy |
| 11,130,760 | B2 | 9/2021 | Yoshino et al. |
| 11,173,158 | B2 | 11/2021 | Hasegawa et al. |
| 11,752,154 | B2 | 9/2023 | Levy |
| 11,773,097 | B2 | 10/2023 | Levy |
| 12,213,982 | B2 | 2/2025 | Levy |
| 12,257,252 | B2 | 3/2025 | Smith et al. |
| 12,269,829 | B2 | 4/2025 | Levy |
| 12,325,706 | B2 | 6/2025 | Yoshino et al. |
| 12,329,757 | B2 | 6/2025 | Smith et al. |
| 2006/0040946 | A1 | 2/2006 | Oppenheimer et al. |
| 2007/0049599 | A1 | 3/2007 | Hesslinger et al. |
| 2007/0270581 | A1 | 11/2007 | Jungles et al. |
| 2008/0075666 | A1 | 3/2008 | Dudley et al. |
| 2010/0130500 | A1 | 5/2010 | Kakkis |
| 2011/0144117 | A1 | 6/2011 | Widmann et al. |
| 2013/0108694 | A1 | 5/2013 | Chou et al. |
| 2013/0197000 | A1 | 8/2013 | Hasegawa et al. |
| 2013/0237543 | A1 | 9/2013 | Oppenheimer et al. |
| 2013/0336975 | A1 | 12/2013 | Dutzar et al. |
| 2015/0119574 | A1 | 4/2015 | Yoshino et al. |
| 2018/0078557 | A1 | 3/2018 | Hasegawa et al. |
| 2019/0308975 | A1 | 10/2019 | Levy |
| 2020/0009145 | A1 | 1/2020 | Hasegawa et al. |
| 2020/0010469 | A1 | 1/2020 | Yoshino et al. |
| 2020/0061070 | A1 | 2/2020 | Levy |
| 2021/0161901 | A1 | 6/2021 | Smith et al. |
| 2021/0220363 | A1 | 7/2021 | Smith et al. |
| 2021/0300930 | A1 | 9/2021 | Levy |
| 2022/0081443 | A1 | 3/2022 | Yoshino et al. |

FOREIGN PATENT DOCUMENTS

| | | | | |
|---|---|---|---|---|
| MX | 2019/006207 | A | 11/2019 | |
| MX | 2020/002271 | A | 10/2020 | |
| WO | WO-2005/028462 | A1 | 3/2005 | |
| WO | WO-2005/049000 | A2 | 6/2005 | |
| WO | WO-2008/128049 | A2 | 10/2008 | |
| WO | WO-2010/072776 | A1 | 7/2010 | |
| WO | WO-2011/132435 | A1 | 10/2011 | |
| WO | WO-2013/168693 | A1 | 11/2013 | |
| WO | WO-2017218421 | A1 * | 12/2017 | ........... A61K 31/519 |
| WO | WO-2018/019931 | A1 | 2/2018 | |
| WO | WO-2018/102314 | A1 | 6/2018 | |
| WO | WO-2018/102315 | A1 | 6/2018 | |
| WO | WO-2018/195321 | A1 | 10/2018 | |
| WO | WO-2019/046849 | A1 | 3/2019 | |
| WO | WO-2021/026247 | A1 | 2/2021 | |
| WO | WO-2021/062264 | A1 | 4/2021 | |

OTHER PUBLICATIONS

Brittain et al., "Polymorphism in Pharmaceutical Solids," CRC Press. 192:3-480 (2016).
Caira M.R., "Crystalline polymorphism of organic compounds." Design of Organic Solids. Topics in Current Chemistry. 198 (1998).
Curtius et al., "Atypical phenylketonuria due to tetrahydrobiopterin deficiency. Diagnosis and treatment with tetrahydrobiopterin, dihydrobiopterin and sepiapterin." Clin Chim Acta. 93(2): 251-62 (1979).
Grant et al., "Relationships among rat ultrasonic vocalizations, behavioral measures of striatal dopamine loss, and striatal tyrosine hydroxylase immunoreactivity at acute and chronic time points following unilateral 6-hydroxydopamine-induced dopamine depletion," Behav Brain Res. 291:361-71 (2015) (24 pages).
Hennermann et al., "Partial and total tetrahydrobiopterin-responsiveness in classical and mild phenylketonuria (PKU)," J Inherit Metab Dis. 25(Suppl 1): 21:041-P (2002) (Abstract only).
Ichiyama et al., "Enzymic studies on the biosynthesis of serotonin in mammalian brain," J Biol Chem. 245(7): 1699-709 (1970).
International Search Report and Written Opinion for International Patent Application No. PCT/US2019/034505, dated Aug. 16, 2019 (13 pages).
Kaufman, "Phenylalanine hydroxylation cofactor in phenylketonuria," Science. 128(3337): 1506-8 (1958).
Klaiman et al., "Tetrahydrobiopterin as a treatment for autism spectrum disorders: a double-blind, placebo-controlled trial," J Child Adolesc Psychopharmacol. 23(5): 320-8 (2013) (11 pages).
Kuplennik et al., "Enhanced nanoencapsulation of sepiapterin within PEG-PCL nanoparticles by complexation with triacetyl-beta cyclodextrin," Molecules. 24(15):2715 (2019).
Kure et al., "Tetrahydrobiopterin-responsive phenylalanine hydroxylase deficiency," J Pediatr. 135(3): 375-8 (1999).
Kwon et al., "Reduced biopterin as a cofactor in the generation of nitrogen oxides by murine macrophages," J Biol Chem. 264(34): 20496-501 (1989).
Matalon et al., "Tetrahydrobiopterin (BH4) responsive phenylalanine hydroxylase (PAH) mutations," J Inherit Metab Dis. 25(Suppl 1): 23:045-P (2002) (Abstract only).
Mayer et al., "Brain nitric oxide snythase is a biopterin- and flavin-containing multi-functional oxido-reductase," FEBS Lett. 288(1-2): 187-91 (1991).
Muntau et al., "Tetrahydrobiopterin as an alternative treatment for mild phenylketonuria," N Engl J Med. 347(26): 2122-32 (2002).
Nagatsu et al., "Tyrosine hydroxylase. The initial step in norepinephrine biosynthesis," J Biol Chem. 239(9): 2910-7 (1964).
Niederwieser et al., "Atypical phenylketonuria with defective biopterin metabolism. Monotherapy with tetrahydrobiopterin or sepiapterin, screening and study of biosynthesis in man," Eur J Pediatr. 138(2): 110-2 (1982).
Park et al., "Optimization of expression conditions enhances production of sepiapterin, a precursor for tetrahydrobiopterin biosynthesis, in recombinant *Escherichia coli*," J Microbiol Biotechnol. 25(10): 1709-13 (2015).
Pfleiderer et al., "Pteridine, LXVIII. Überführung von biopterin in sepiapterin und absolute konfiguration des sepiapterins," Chem Ber. 112: 2750-2755 (1979).
Ponzone et al., "Hyperphenylalaninemia and pterin metabolism in serum and erythrocytes," Clin Chim Acta. 216(1-2): 63-71 (1993).
Saeed et al., "Uncertainty of thermal characterization of phase change material by differential scanning calorimetry analysis," Int J Eng Res Technol. 5(1): 405-12 (2016).
Sawabe et al., "Cellular uptake of sepiapterin and push-pull accumulation of tetrahydrobiopterin," Mol Genet Metab. 94(4): 410-6 (2008).
Sawabe et al., Sepiapterin administration raises tissue BH4 levels more efficiently than BH4 supplement in normal mice, *Chemistry and Biology of Pteridines and Folates*. Ed. Milstien et al., pp. 199-204 (2001).
Schircks et al., "Herstellung von (6 R, S)-5,6,7,8-Tetrahydro-L-biopterin, 7,8-Dihydro-L-biopterin, L-Sepiapterin, Deoxysepiapterin, (6 R, S)-5,6-Dihydrodeoxysepiapterin und 2'-Deoxybiopterin," Helvetica Chimica Acta. 61(7): 2731-2738 (1978).
Shircks Laboratories, "Data Sheet: L-Sepiapterin. Product No. 11.225," published Jan. 26, 2016 (1 page).
Smith et al., "Phase I clinical evaluation of CNSA-001 (sepiapterin), a novel pharmacological treatment for phenylketonuria and tetrahydrobiopterin deficiencies, in healthy volunteers," Mol Genet Metab. 126(4): 406-12 (2019).
Spaapen et al., "Tetrahydrobiopterin-responsive phenylalanine hydroxylase deficiency, state of the art," Mol Genet Metab. 78(2): 93-9 (2003).
Sugiura et al., "The structures of the reoxidation products of 7,8-dihydroneopterin," Bull Chem Soc Jpn. 46(3): 939-42 (1973).
Tietz et al., "A new pteridine-requiring enzyme system for the oxidiation of glyceryl ethers," J Biol Chem. 239(12): 4081-90 (1964).
Woo et al., "Production of sepiapterin in *Escherichia coli* by coexpression of cyanobacterial GTP cyclohydrolase I and human 6-pyruvoyltetrahydropterin synthase," Appl Environ Microbiol. 68(6): 3138-3140 (2002).

(56) References Cited

OTHER PUBLICATIONS

NORD "Tetrahydrobiopterin Deficiency," (online PD Sep. 2016).
Clinical Trials "A Study of CNSA-001 in Primary Tetrahydrobiopterin (BH4) Deficient Participants with Hyperphenylalaninemia," (printed on Feb. 11, 2021).
Singhal et al., "Drug polymorphism and dosage form design: a practical perspective." Adv Drug Deliv Rev. 56(3): 335-47 (2004).
Balbach et al., "Pharmaceutical evaluation of early development candidates 'the 100 mg-approach'," Int J Pharm. 275(1-2):1-12 (2004).
"Pharmaceutical Dosage Forms: Tablets" edited by Larry L. Augsburger, Stephen W. Hoag, 3rd edition, vol. 2, chapter 2, p. 62-67 (2008) (11 pages).
Bastin et al., "Salt Selection and Optimisation Procedures for Pharmaceutical New Chemical Entities," Org Proc Res Dev. 4(5):427-35 (Jul. 2000) (10 pages).
Duggirala et al., "Pharmaceutical cocrystals: along the path to improved medicines." Chem Commun. 52(4):640-655 (Jan. 2016) (17 Pages).
Guillory, Chapter 5: Generation of Polymorphs, Hydrates, Solvates, and Amorphous Solids, *Polymorphism in Pharmaceutical Solids*. ed. Harry G. Brittain, Marcel Dekker, Inc., New York, pp. 183-226 (1999) (44 pages).
Haynes et al., "Occurrence of pharmaceutically acceptable anions and cations in the Cambridge Structural Database," J Pharm Sci. 94(10):2111-20 (Oct. 2005).
Stahl, Preparation of water-soluble compounds through salt formation. *The Practice of Medicinal Chemistry, 2nd edition*, p. 601-615 (2003).
Gould, "Salt selection for basic drugs," Int J Pharm. 33(1-3):201-217 (Nov. 1986) (17 pages).
Paulekuhn et al., "Trends in active pharmaceutical ingredient salt selection based on analysis of the Orange Book database," J Med Chem. 50(26): 6665-72 (Dec. 2007) (8 pages).
Thakuria et al., "Crystal Polymorphism in Pharmaceutical Science," Comprehensive Supramolecular Chemistry II. vol. 5, Chapter 22 (Jun. 2017) (29 pages).
Lee et al., "Crystal polymorphism in chemical process development," Annu Rev Chem Biomol Eng. 2:259-80 (Jul. 2011).
Martin, "Let's not forget tautomers," J Computer Aided Mol Des. 23(10):693-704 (Oct. 2009).
NCBI, "PubChem Structure Search Help," <https://pubchem.ncbi.nlm.nih.gov/search/help_search.html>, accessed Nov. 1, 2024 (13 pages).
Spyrakis et al., "Correct protonation states and relevant waters = better computational simulations?" Curr Pharm Des. 19(23):4291-309 (2013).
Abell et al., "Effect of oral CNSA-001 (sepiapterin, PTC923) on gastric accommodation in women with diabetic gastroparesis: a randomized, placebo-controlled, phase 2 trial," J Diabetes Complications. 35(9):107961 (2021) (7 pages).
Bratkovic et al., "PTC923 (sepiapterin) lowers elevated blood phenylalanine in subjects with phenylketonuria: a phase 2 randomized, multi-center, three-period crossover, open-label, active controlled, all-comers study," Metabolism. 128:155116 (2022) (8 pages).
Extended European Search Report for European Patent Application No. 19811127.0, dated Mar. 10, 2022 (11 pages).
Office Action for Japanese Patent Application No. 2019-548533, mailed Oct. 26, 2021 (10 pages).
Office Action for Japanese Patent Application No. 2019-548534, dated Nov. 2, 2021 (10 pages).
Ono, "Analysis of salt selection of current active pharmaceutical ingredients (API)," Yakuzaigaku. 73(3):176-182 (2013) (8 pages), Concise explanation of revelance only.
Opladen et al., "Consensus guideline for the diagnosis and treatment of tetrahydrobiopterin ($BH_4$) deficiencies." Orphanet J Rare Dis. 15(1):126 (2020) (30 pages).
Shircks Laboratories, "Data Sheet: Tetrahydrobioterin Tablets," published Jul. 1, 2009 (1 page).
Smith et al., "Exploratory study of the effect of one week of orally administered CNSA-001 (sepiapterin) on CNS levels of tetrahydrobiopterin, dihydrobiopterin and monoamine neurotransmitter metabolites in healthy volunteers," Mol Genet Metab Rep. 21:100500 (2019) (3 pages).
Takada, "API form screening and selection in drug discovery stage," Pharm Stage. 6(10):20-25 (2007) (9 pages), Concise explanation of revelance only.
Yoshinaki, *Organic compound crystal production handbook*. 10-11, 57-73, 78-81 (2008) (13 pages), Concise explanation of revelance only.
Byrn et al., "Pharmaceutical Solids: A Strategic Approach to Regulatory Considerations", *Pharmaceutical Research*, 12(7): 945-954 (Jul. 1995) (10 pages).
Carlson et al., "An integrated high throughput workflow for preformulations: Polymorph and salt selection studies", *Pharm. Chem, Drug Development*. pp. 10-15 (Jul. 2003) (6 pages).
English Translation of Decision of Refusal in JP Application No. 2022-151886 dated Jan. 16, 2024 (4 pages).
Kazuhide Ashizawa et al., "Preformulation Studies on the Drug Discovery Stage," Pharm Stage. 9(6):72-79 (2009) (10 pages).
Office Action and Examiner Search Report issued in CA 3,102,070 dated Apr. 4, 2024 (11 pages).
Ono, "A crystalline form screening of medicines," Pharmacia. 47(11):1014-18 (2011) (6 pages).
The Japanese Pharmacopoeia. 17th ed. The Ministry of Health, Labour and Welfare; Tokyo, Japan, pp. 71-74 (Jan. 7, 2016) (10 pages).
Yamano, "Process research of new medicines, polymorphism of crystal," Pharmacia. 45(4):327-32 (2009) (7 pages).
Yoshinaki, "Organic compound crystal production handbook," 57-85 (Jan. 2008) (17 pages).

* cited by examiner

PHARMACEUTICALLY ACCEPTABLE SALTS OF SEPIAPTERIN

BACKGROUND OF THE INVENTION

Primary tetrahydrobiopterin deficiency (PBD) is caused by deficiency of GTP cyclohydrolase I (GTP-CH), 6-pyruvoyl-tetrahydropterin synthase (PTPS), or sepiapterin reductase (SR) that impair the biosynthesis of tetrahydrobiopterin (BH4) or by defects in BH4 recycling (pterin-4a-carbinolamine dehydratase (PCD) or dihydropteridine reductase (DHPR) deficiency). PBD accounts for 1 to 3% of all cases of hyperphenylalaninemia (HPA), with virtually all of the remaining cases due to phenylalanine hydroxylase deficiency.

BH4 is an essential cofactor for phenylalanine hydroxylase, tyrosine hydroxylase, tryptophan hydroxylase, fatty acid glycerylether oxygenase, and nitric oxide (NO) synthase.

In PBD, impaired hydroxylation of Phenylalanine (Phe) to Tyrosine (Tyr) results in HPA. The reduced synthesis of Tyr and impaired activities of Tyr and tryptophan hydroxylases results in reduced formation of neurotransmitters and consequent neuromotor deficits.

Phenotypically, BH4 deficiency presents with HPA and deficiency of the neurotransmitter precursors, L-dopa and 5-hydroxytryptophan, and thus may be detected through screening programs which measure Phe in order to detect phenylalanine hydroxylase deficiency (the exception being SR deficient patients who have normal Phe concentrations).

Current treatment of BH4 deficiency consists of reducing Phe concentrations in blood either by oral administration of BH4 (in GTP-CH and PTPS deficiency) and/or low Phe diet (mainly in DHPR deficiency) and administration of the neurotransmitter precursors L-dopa and 5-hydroxytryptophan (5HTP).

Reports of long-term follow-up of patients with BH4 deficiency are scarce. Therapeutic strategies vary by treating physician and clinic, are far from clinically based evidence, and include pharmacologic agents none of which have marketing approval for this indication. Therefore, a need exists for new therapies for BH4 deficiency.

SUMMARY OF THE INVENTION

The present invention features new pharmaceutical salts of sepiapterin which exhibit improved physical properties. In particular, the invention features salts of sepiapterin with improved stability, such as nicotinate, phosphate, tartrate, fumarate, or hydrochloride. The invention also features pharmaceutical compositions including a pharmaceutically effective amount of one or more salts of sepiapterin, as well as methods of treating tetrahydrobiopterin-related disorders including administration of a sepiapterin salt of the invention to a subject in need thereof.

In an aspect, the invention features a salt and/or co-crystal of sepiapterin. In some embodiments, the salt and/or co-crystal of sepiapterin is the methanesulfonate salt and/or co-crystal, the nicotinate salt and/or co-crystal, the p-toluenesulfonate salt and/or co-crystal, the benzenesulfonate salt and/or co-crystal, the phosphate salt and/or co-crystal (e.g., a 1:1 phosphate salt and/or co-crystal, i.e., one molecule of sepiapterin to one molecule phosphate), the malonate salt and/or co-crystal (e.g., a 1:1 malonate salt and/or co-crystal, i.e., one molecule of sepiapterin to one molecule malonate), the tartrate salt and/or co-crystal (e.g., a 1:1 tartrate salt and/or co-crystal, i.e., one molecule of sepiapterin to one molecule tartrate), the gentisate salt and/or co-crystal (e.g., a 2:1 gentisate salt and/or co-crystal, i.e., two molecules of sepiapterin to one molecule gentisate), the fumarate salt and/or co-crystal (e.g., a 2:1 fumarate salt and/or co-crystal, i.e., two molecules of sepiapterin to one molecule fumarate), the glycolate salt and/or co-crystal (e.g., a 3:1 glycolate salt and/or co-crystal, i.e., three molecules of sepiapterin to one molecule glycolate), the acetate salt and/or co-crystal, or the sulfate salt and/or co-crystal (e.g., a 2:1 sulfate salt and/or co-crystal, i.e., two molecules of sepiapterin to one molecule sulfate). In some embodiments, the salt is a co-crystal with the acid. In some embodiments, the salt and/or co-crystal of sepiapterin have improved properties, e.g., improved stability, purity, exposure, and/or bioavailability.

In some embodiments, the salt and/or co-crystal of sepiapterin is the methanesulfonate salt and/or co-crystal.

In some embodiments, the salt and/or co-crystal of sepiapterin is the nicotinate salt and/or co-crystal.

In some embodiments, the salt and/or co-crystal of sepiapterin is the p-toluenesulfonate salt and/or co-crystal.

In some embodiments, the salt and/or co-crystal of sepiapterin is the benzenesulfonate salt and/or co-crystal.

In some embodiments, the salt and/or co-crystal of sepiapterin is the phosphate salt and/or co-crystal, wherein the phosphate counterion is $H_2PO_4^-$. In some embodiments, the salt and/or co-crystal of sepiapterin is the phosphate salt and/or co-crystal, wherein the phosphate counterion is $HPO_4^{2-}$. In some embodiments, the salt and/or co-crystal of sepiapterin is the phosphate salt and/or co-crystal, wherein the phosphate counterion is $PO_4^{3-}$. In some embodiments, the salt and/or co-crystal of sepiapterin is the 1:1 phosphate salt and/or co-crystal, i.e., one molecule of sepiapterin to one molecule phosphate. In some embodiments, the salt and/or co-crystal of sepiapterin is the 2:1 phosphate salt and/or co-crystal, i.e., two molecules of sepiapterin to one molecule phosphate.

In some embodiments, the salt and/or co-crystal of sepiapterin is the 1:1 malonate salt and/or co-crystal, i.e., one molecule of sepiapterin to one molecule malonate. In some embodiments, the salt and/or co-crystal of sepiapterin is the 2:1 malonate salt and/or co-crystal, i.e., two molecules of sepiapterin to one molecule malonate.

In some embodiments, the salt and/or co-crystal of sepiapterin is the 1:1 tartrate salt and/or co-crystal, i.e., one molecule of sepiapterin to one molecule tartrate. In some embodiments, the salt and/or co-crystal of sepiapterin is the 2:1 tartrate salt and/or co-crystal, i.e., two molecules of sepiapterin to one molecule tartrate.

In some embodiments, the salt and/or co-crystal of sepiapterin is the 1:1 gentisate salt and/or co-crystal, i.e., one molecule of sepiapterin to one molecule gentisate. In some embodiments, the salt and/or co-crystal of sepiapterin is the 2:1 gentisate salt and/or co-crystal, i.e., two molecules of sepiapterin to one molecule gentisate.

In some embodiments, the salt and/or co-crystal of sepiapterin is the 1:1 fumarate salt and/or co-crystal, i.e., one molecule of sepiapterin to one molecule fumarate. In some embodiments, the salt and/or co-crystal of sepiapterin is the 2:1 fumarate salt and/or co-crystal, i.e., two molecules of sepiapterin to one molecule fumarate.

In some embodiments, the salt and/or co-crystal of sepiapterin is the 1:1 glycolate salt and/or co-crystal, i.e., one molecule of sepiapterin to one molecule glycolate. In some embodiments, the salt and/or co-crystal of sepiapterin is the 2:1 glycolate salt and/or co-crystal, i.e., two molecules of sepiapterin to one molecule glycolate. In some embodiments, the salt and/or co-crystal of sepiapterin is the 3:1 glycolate salt and/or co-crystal, i.e., three molecules of sepiapterin to one molecule glycolate.

In some embodiments, the salt and/or co-crystal of sepiapterin is the sulfate salt and/or co-crystal, wherein the sulfate counterion is $HSO_4^-$. In some embodiments, the salt and/or co-crystal of sepiapterin is the sulfate salt and/or co-crystal, wherein the sulfate counterion is $SO_4^{2-}$. In some embodiments, the salt and/or co-crystal of sepiapterin is the 1:1 sulfate salt and/or co-crystal, i.e., one molecule of sepiapterin to one molecule sulfate. In some embodiments, the salt and/or co-crystal of sepiapterin is the 2:1 sulfate salt and/or co-crystal, i.e., two molecules of sepiapterin to one molecule sulfate.

In some embodiments, the salt and/or co-crystal of sepiapterin is the acetate salt and/or co-crystal.

In some embodiments, the pharmaceutically acceptable salt and/or co-crystal is crystalline. In some embodiments, the pharmaceutically acceptable salt and/or co-crystal includes less than 40% by weight (e.g., less than 30%, less than 20%, less than 10%, less than 5%, less than 1% or between 30-40%, 25-35%, 20-30%, 15-25%, 10-20%, 5-15%, or 1-10%) of amorphous compound. In some embodiments, the pharmaceutically acceptable salt and/or co-crystal is substantially free of amorphous compound. In some embodiments, the pharmaceutically acceptable salt and/or co-crystal is substantially free of any other salt or crystal form of sepiapterin.

In some embodiments, the pharmaceutically acceptable salt and/or co-crystal is stable. For example, in some embodiments, upon exposure to 25° C. and 60% relative humidity and/or 40° C. and 75% relative humidity for two weeks, the pharmaceutically acceptable salt and/or co-crystal remains at least 90% pure (e.g., at least 95% pure, at least 96% pure, at least 97% pure, at least 98% pure, at least 99% pure) and/or does not undergo a form change (e.g., the salt and/or co-crystal remains substantially free of the free base and/or there is no polymorph form change of the salt and/or co-crystal and/or the free base).

In some embodiments, the pharmaceutically acceptable salt and/or co-crystal results in increased (e.g., increased at least 5%, at least 10%, at least 15%, at least 25%, at least 50%, at least 75%, at least 95%, at least 99%, at least 100%) exposure in a subject (e.g., increased exposure as measured by BH4 and/or sepiapterin levels in the plasma, CSF, and/or brain of the subject) compared with other salts and/or co-crystals of sepiapterin and/or sepiapterin free base.

In some embodiments, the pharmaceutically acceptable salt and/or co-crystal results in increased (e.g., increased at least 5%, at least 10%, at least 15%, at least 25%, at least 50%, at least 75%, at least 95%, at least 99%, at least 100%) bioavailability in a subject compared with other salts and/or co-crystals of sepiapterin and/or sepiapterin free base.

In some embodiments, the pharmaceutically acceptable salt and/or co-crystal has improved crystallinity compared to other salts and/or co-crystals of sepiapterin and/or sepiapterin free base.

In some embodiments, the pharmaceutically acceptable salt and/or co-crystal of sepiapterin is a hydrochloride salt and/or co-crystal. In some embodiments, the hydrochloride salt and/or co-crystal has an endothermic onset at about 218° C. (e.g., from 216° C. to 220° C., such as 217° C. to 219° C.) in differential scanning calorimetry (DSC) profile. In some embodiments, the hydrochloride salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the hydrochloride salt and/or co-crystal has at least one peak at diffraction angle 2θ(°) of 7.8±0.5 as measured by X-ray powder diffractometry. In some embodiments, the hydrochloride salt and/or co-crystal further has at least one peak at diffraction angle 2θ(°) of 7.8±0.5, 12.9±0.5, and/or 26.2±0.5 as measured by X-ray powder diffractometry. In some embodiments, the hydrochloride salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 1 as measured by X-ray powder diffractometry. In some embodiments, the hydrochloride salt and/or co-crystal has all of the peaks listed in Table 1 as measured by X-ray powder diffractometry.

TABLE 1

XRPD peak list for the hydrochloride salt and/or co-crystal of sepiapterin

| 2θ (°) | Intensity |
|---|---|
| 7.8 | 100.00 |
| 8.9 | 6.89 |
| 12.9 | 58.56 |
| 15.6 | 8.52 |
| 17.9 | 25.23 |
| 19.2 | 5.48 |
| 21.1 | 10.97 |
| 23.6 | 25.15 |
| 25.2 | 22.66 |
| 26.2 | 45.91 |
| 27.6 | 32.94 |
| 30.3 | 10.50 |
| 31.7 | 7.83 |
| 34.2 | 8.87 |
| 36.7 | 3.67 |

In some embodiments, the pharmaceutically acceptable salt and/or co-crystal of sepiapterin is a methanesulfonate salt and/or co-crystal. In some embodiments, the methanesulfonate salt and/or co-crystal has an endothermic onset at about 182° C. (e.g., from 180° C. to 184° C., such as 181° C. to 183° C.) in differential scanning calorimetry (DSC) profile. In some embodiments, the methanesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the methanesulfonate salt and/or co-crystal has at least one peak at diffraction angle 2θ(°) of 23.5±0.5 as measured by X-ray powder diffractometry. In some embodiments, the methanesulfonate salt and/or co-crystal further has at least one peak at diffraction angle 2θ(°) of 7.9±0.5, 23.5±0.5, and/or 29.0±0.5 as measured by X-ray powder diffractometry. In some embodiments, the methanesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 2 as measured by X-ray powder diffractometry. In some embodiments, the methanesulfonate salt and/or co-crystal has all of the peaks listed in Table 2 as measured by X-ray powder diffractometry.

TABLE 2

| XRPD peak list for the methanesulfonate salt and/or co-crystal Form 1 of sepiapterin | |
|---|---|
| 2θ (°) | Intensity |
| 7.9 | 21.77 |
| 11.7 | 8.20 |
| 13.7 | 8.52 |
| 15.7 | 4.79 |
| 16.6 | 5.34 |
| 18.0 | 5.66 |
| 19.8 | 2.10 |
| 20.3 | 5.36 |
| 20.9 | 2.43 |
| 22.3 | 4.25 |
| 22.7 | 2.15 |
| 23.5 | 100.00 |
| 24.7 | 3.69 |
| 25.6 | 2.70 |
| 26.8 | 1.79 |
| 27.2 | 1.68 |
| 28.3 | 2.75 |
| 29.0 | 57.60 |
| 29.8 | 5.18 |
| 30.5 | 1.37 |
| 32.2 | 4.66 |
| 33.0 | 1.64 |
| 36.5 | 1.29 |

In some embodiments, the methanesulfonate salt and/or co-crystal has at least one peak at diffraction angle 2θ(°) of 7.9±0.5 as measured by X-ray powder diffractometry. In some embodiments, the methanesulfonate salt and/or co-crystal further has at least one peak at diffraction angle 2θ(°) of 7.9±0.5, 23.4±0.5, and/or 28.9±0.5 as measured by X-ray powder diffractometry. In some embodiments, the methanesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 3 as measured by X-ray powder diffractometry. In some embodiments, the methanesulfonate salt and/or co-crystal has all of the peaks listed in Table 3 as measured by X-ray powder diffractometry.

TABLE 3

| XRPD peak list for the methanesulfonate salt and/or co-crystal Form 2 of sepiapterin | |
|---|---|
| 2θ (°) | Intensity |
| 7.9 | 100.00 |
| 11.0 | 21.32 |
| 12.1 | 22.02 |
| 13.5 | 79.87 |
| 15.7 | 11.87 |
| 17.8 | 9.81 |
| 19.7 | 10.93 |
| 21.3 | 26.79 |
| 23.4 | 96.13 |
| 24.1 | 24.88 |
| 24.3 | 22.10 |
| 25.5 | 9.45 |
| 26.0 | 11.27 |
| 27.6 | 7.63 |
| 28.9 | 95.64 |
| 31.2 | 4.39 |
| 36.1 | 6.65 |

In some embodiments, the pharmaceutically acceptable salt and/or co-crystal of sepiapterin is a nicotinate salt and/or co-crystal. In some embodiments, the nicotinate salt and/or co-crystal has an endothermic onset at about 220° C. (e.g., from 218° C. to 222° C., such as 219° C. to 221° C.) in differential scanning calorimetry (DSC) profile. In some embodiments, the nicotinate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the nicotinate salt and/or co-crystal has at least one peak at diffraction angle 2θ(°) of 24.5±0.5 as measured by X-ray powder diffractometry. In some embodiments, the nicotinate salt and/or co-crystal further has at least one peak at diffraction angle 2θ(°) of 9.9±0.5, 23.2±0.5, and/or 24.5±0.5 as measured by X-ray powder diffractometry. In some embodiments, the nicotinate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 4 as measured by X-ray powder diffractometry. In some embodiments, the nicotinate salt and/or co-crystal has all of the peaks listed in Table 4 as measured by X-ray powder diffractometry.

TABLE 4

| XRPD peak list for the nicotinate salt and/or co-crystal of sepiapterin | |
|---|---|
| 2θ (°) | Intensity |
| 9.5 | 10.29 |
| 9.9 | 53.95 |
| 11.5 | 9.31 |
| 12.0 | 11.76 |
| 14.7 | 14.20 |
| 15.9 | 17.61 |
| 17.5 | 7.53 |
| 19.0 | 5.37 |
| 20.8 | 5.88 |
| 21.3 | 6.12 |
| 21.7 | 7.20 |
| 23.2 | 34.05 |
| 24.5 | 100.00 |
| 25.2 | 12.90 |
| 28.0 | 8.51 |
| 31.1 | 5.39 |
| 32.3 | 4.52 |
| 33.4 | 8.02 |
| 35.1 | 5.05 |

In some embodiments, the pharmaceutically acceptable salt and/or co-crystal of sepiapterin is a toluenesulfonate salt. In some embodiments, the toluenesulfonate salt and/or co-crystal has an endothermic onset at about 190° C. (e.g., from 188° C. to 192° C., such as 189° C. to 191° C.) and/or 263° C. (e.g., from 261° C. to 265° C., such as 262° C. to 264° C.) in differential scanning calorimetry (DSC) profile. In some embodiments, the toluenesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the toluenesulfonate salt and/or co-crystal has at least one peak at diffraction angle 2θ(°) of 6.5±0.5 as measured by X-ray powder diffractometry. In some embodiments, the toluenesulfonate salt and/or co-crystal further has at least one peak at diffraction angle 2θ(°) of 6.5±0.5, 15.1±0.5, and/or 23.4±0.5 as measured by X-ray powder diffractometry. In some embodiments, the toluenesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 5 as measured by X-ray powder diffractometry. In some embodiments, the toluenesulfonate salt and/or co-crystal has all of the peaks listed in Table 5 as measured by X-ray powder diffractometry.

TABLE 5

XRPD peak list for the toluenesulfonate salt and/or co-crystal of sepiapterin

| 2θ (°) | Intensity |
|---|---|
| 6.5 | 100.00 |
| 12.9 | 1.79 |
| 14.3 | 1.39 |
| 15.1 | 15.36 |
| 16.2 | 5.33 |
| 18.4 | 8.96 |
| 19.6 | 3.06 |
| 20.2 | 4.86 |
| 21.8 | 2.23 |
| 22.5 | 2.95 |
| 23.1 | 7.99 |
| 23.4 | 9.14 |
| 24.5 | 1.81 |
| 26.0 | 2.48 |
| 27.0 | 4.49 |
| 27.3 | 3.93 |
| 28.1 | 5.31 |
| 28.4 | 5.59 |
| 28.8 | 2.05 |
| 30.6 | 2.24 |
| 31.0 | 1.98 |
| 32.6 | 1.82 |

In some embodiments, the pharmaceutically acceptable salt and/or co-crystal of sepiapterin is a benzenesulfonate salt and/or co-crystal. In some embodiments, the benzenesulfonate salt and/or co-crystal has an endothermic onset at about 193° C. (e.g., from 191° C. to 195° C., such as 192° C. to 194° C.) and/or 206° C. (e.g., from 204° C. to 208° C., such as 205° C. to 207° C.) in differential scanning calorimetry (DSC) profile. In some embodiments, the benzenesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the benzenesulfonate salt and/or co-crystal has at least one peak at diffraction angle 2θ(°) of 6.5±0.5 as measured by X-ray powder diffractometry. In some embodiments, the benzenesulfonate salt and/or co-crystal further has at least one peak at diffraction angle 2θ(°) of 6.5±0.5, 14.8±0.5, and/or 19.6±0.5 as measured by X-ray powder diffractometry. In some embodiments, the benzenesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 6 as measured by X-ray powder diffractometry. In some embodiments, the benzenesulfonate salt and/or co-crystal has all of the peaks listed in Table 6 as measured by X-ray powder diffractometry.

TABLE 6

XRPD peak list for the benzenesulfonate salt and/or co-crystal of sepiapterin

| 2θ (°) | Intensity |
|---|---|
| 4.9 | 5.90 |
| 6.5 | 100.00 |
| 14.8 | 16.73 |
| 17.8 | 4.23 |
| 19.6 | 7.98 |
| 21.5 | 2.49 |
| 23.7 | 3.46 |
| 24.5 | 3.84 |
| 26.1 | 3.29 |

In some embodiments, the pharmaceutically acceptable salt and/or co-crystal of sepiapterin is a sulfate salt. In some embodiments, the sulfate salt and/or co-crystal has an endothermic onset at about 196° C. (e.g., from 194° C. to 198° C., such as 195° C. to 197° C.) in differential scanning calorimetry (DSC) profile. In some embodiments, the sulfate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the sulfate salt and/or co-crystal has at least one peak at diffraction angle 2θ(°) of 5.1±0.5 as measured by X-ray powder diffractometry. In some embodiments, the sulfate salt and/or co-crystal further has at least one peak at diffraction angle 2θ(°) of 5.1±0.5, 7.8±0.5, and/or 23.0±0.5 as measured by X-ray powder diffractometry. In some embodiments, the sulfate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 7 as measured by X-ray powder diffractometry. In some embodiments, the sulfate salt and/or co-crystal has all of the peaks listed in Table 7 as measured by X-ray powder diffractometry.

TABLE 7

XRPD peak list for the sulfate salt and/or co-crystal of sepiapterin

| 2θ (°) | Intensity |
|---|---|
| 5.1 | 100.00 |
| 6.8 | 3.33 |
| 7.8 | 43.48 |
| 10.2 | 15.92 |
| 15.7 | 18.13 |
| 17.2 | 8.33 |
| 18.7 | 6.49 |
| 19.8 | 5.19 |
| 21.3 | 5.52 |
| 23.0 | 19.05 |
| 23.5 | 8.29 |
| 24.2 | 5.59 |
| 24.8 | 17.44 |
| 25.7 | 4.97 |
| 26.7 | 10.38 |
| 28.7 | 11.49 |
| 30.4 | 2.88 |
| 31.0 | 3.67 |

In some embodiments, the pharmaceutically acceptable salt and/or co-crystal of sepiapterin is a phosphate salt. In some embodiments, the phosphate salt and/or co-crystal has an endothermic onset at about 144° C. (e.g., from 142° C. to 146° C., such as 143° C. to 145° C.) and/or 207° C. (e.g., from 205° C. to 209° C., such as 206° C. to 208° C.) in differential scanning calorimetry (DSC) profile. In some embodiments, the phosphate salt and/or co-crystal has a loss of weight from 31° C. to 150° C. of less than 12% (e.g., less than 10%, less than 5%, less than 2%, or less than 1%) as measured by thermal gravimetric analysis.

In some embodiments, the phosphate salt and/or co-crystal has at least one peak at diffraction angle 2θ(°) of 25.6±0.5 as measured by X-ray powder diffractometry. In some embodiments, the phosphate salt and/or co-crystal further has at least one peak at diffraction angle 2θ(°) of 16.6±0.5, 22.2±0.5, and/or 25.6±0.5 as measured by X-ray powder diffractometry. In some embodiments, the phosphate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 8 as measured by X-ray powder diffractometry. In some embodiments, the phosphate salt and/or co-crystal has all of the peaks listed in Table 8 as measured by X-ray powder diffractometry.

TABLE 8

XRPD peak list for the phosphate salt and/or co-crystal of sepiapterin

| 2θ (°) | Intensity |
|---|---|
| 5.5 | 4.41 |
| 8.1 | 1.21 |
| 8.9 | 2.21 |
| 10.3 | 1.79 |
| 10.8 | 5.80 |
| 15.3 | 1.84 |
| 16.6 | 8.35 |
| 17.7 | 1.95 |
| 20.3 | 1.40 |
| 21.2 | 1.61 |
| 22.2 | 9.77 |
| 23.1 | 1.74 |
| 25.6 | 100.00 |
| 30.8 | 6.31 |
| 31.1 | 4.85 |
| 33.5 | 0.73 |
| 36.0 | 1.70 |

In some embodiments, the pharmaceutically acceptable salt and/or co-crystal of sepiapterin is a malonate salt and/or co-crystal. In some embodiments, the malonate salt and/or co-crystal has an endothermic onset at about 175° C. (e.g., from 173° C. to 177° C., such as 174° C. to 176° C.) in differential scanning calorimetry (DSC) profile. In some embodiments, the malonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the malonate salt and/or co-crystal has at least one peak at diffraction angle 2θ(°) of 6.9±0.5 as measured by X-ray powder diffractometry. In some embodiments, the malonate salt and/or co-crystal further has at least one peak at diffraction angle 2θ(°) of 6.9±0.5, 23.8±0.5, and/or 25.5±0.5 as measured by X-ray powder diffractometry. In some embodiments, the malonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 9 as measured by X-ray powder diffractometry. In some embodiments, the malonate salt and/or co-crystal has all of the peaks listed in Table 9 as measured by X-ray powder diffractometry.

TABLE 9

XRPD peak list for the malonate salt and/or co-crystal of sepiapterin

| 2θ (°) | Intensity |
|---|---|
| 6.9 | 100.00 |
| 8.4 | 13.11 |
| 10.6 | 7.62 |
| 16.4 | 5.63 |
| 17.8 | 9.73 |
| 19.3 | 8.96 |
| 20.1 | 9.99 |
| 22.2 | 10.50 |
| 22.7 | 20.52 |
| 23.8 | 34.02 |
| 24.5 | 5.82 |
| 25.5 | 24.50 |
| 26.6 | 4.00 |
| 27.3 | 6.96 |
| 29.8 | 5.38 |
| 33.1 | 12.08 |

In some embodiments, the pharmaceutically acceptable salt and/or co-crystal of sepiapterin is a tartrate salt (e.g., an L-tartrate salt). In some embodiments, the tartrate salt and/or co-crystal has an endothermic onset at about 156° C. (e.g., from 154° C. to 158° C., such as 155° C. to 157° C.) and/or 175° C. (e.g., from 173° C. to 177° C., such as 174° C. to 176° C.) in differential scanning calorimetry (DSC) profile. In some embodiments, the tartrate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the tartrate salt and/or co-crystal has at least one peak at diffraction angle 2θ(°) of 7.4±0.5 as measured by X-ray powder diffractometry. In some embodiments, the tartrate salt and/or co-crystal further has at least one peak at diffraction angle 2θ(°) of 7.4±0.5, 21.8±0.5, and/or 23.9±0.5 as measured by X-ray powder diffractometry. In some embodiments, the tartrate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 10 as measured by X-ray powder diffractometry. In some embodiments, the tartrate salt and/or co-crystal has all of the peaks listed in Table 10 as measured by X-ray powder diffractometry.

TABLE 10

XRPD peak list for the L-tartrate salt and/or co-crystal of sepiapterin

| 2θ (°) | Intensity |
|---|---|
| 7.4 | 100.00 |
| 10.1 | 47.99 |
| 14.2 | 82.76 |
| 14.7 | 27.06 |
| 19.1 | 21.16 |
| 20.2 | 29.91 |
| 21.8 | 85.30 |
| 22.1 | 53.68 |
| 23.9 | 85.30 |
| 24.9 | 19.26 |
| 25.5 | 28.45 |
| 26.8 | 18.58 |
| 29.7 | 21.59 |
| 31.6 | 10.10 |
| 32.9 | 22.18 |

In some embodiments, the pharmaceutically acceptable salt and/or co-crystal of sepiapterin is a fumarate salt and/or co-crystal. In some embodiments, the fumarate salt and/or co-crystal has an endothermic onset at about 77° C. (e.g., from 75° C. to 79° C., such as 76° C. to 78° C.), 133° C. (e.g., from 131° C. to 135° C., such as 132° C. to 134° C.), and/or 190° C. (e.g., from 188° C. to 192° C., such as 189° C. to 191° C.) in differential scanning calorimetry (DSC) profile. In some embodiments, the fumarate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the fumarate salt and/or co-crystal has at least one peak at diffraction angle 2θ(°) of 24.0±0.5 as measured by X-ray powder diffractometry. In some embodiments, the fumarate salt and/or co-crystal further has at least one peak at diffraction angle 2θ(°) of 11.4±0.5, 11.9±0.5, and/or 24.0±0.5 as measured by X-ray powder diffractometry. In some embodiments, the fumarate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 11 as measured by X-ray powder diffractometry. In some embodiments, the fumarate salt and/or co-crystal has all of the peaks listed in Table 11 as measured by X-ray powder diffractometry.

TABLE 11

XRPD peak list for the fumarate salt and/or co-crystal of sepiapterin

| 2θ (°) | Intensity |
|---|---|
| 6.1 | 6.43 |
| 7.7 | 5.40 |
| 11.4 | 53.62 |
| 11.9 | 33.37 |
| 14.2 | 8.03 |
| 16.5 | 6.70 |
| 18.3 | 13.86 |
| 19.0 | 6.68 |
| 20.7 | 10.02 |
| 21.3 | 7.02 |
| 22.8 | 24.68 |
| 24.0 | 100.00 |
| 28.3 | 33.26 |
| 32.7 | 6.35 |
| 36.0 | 3.28 |
| 38.5 | 6.02 |

In some embodiments, the pharmaceutically acceptable salt and/or co-crystal of sepiapterin is a gentisate salt and/or co-crystal. In some embodiments, the gentisate salt and/or co-crystal has an endothermic onset at about 83° C. (e.g., from 81° C. to 85° C., such as 82° C. to 84° C.), 134° C. (e.g., from 132° C. to 136° C., such as 133° C. to 135° C.), and/or 149° C. (e.g., from 147° C. to 151° C., such as 148° C. to 150° C.) in differential scanning calorimetry (DSC) profile. In some embodiments, the gentisate salt and/or co-crystal has a loss of weight from 31° C. to 150° C. of less than 7% (e.g., less than 5%, less than 3%, less than 2%, or less than 1%) as measured by thermal gravimetric analysis.

In some embodiments, the gentisate salt and/or co-crystal has at least one peak at diffraction angle 2θ(°) of 7.1±0.5 as measured by X-ray powder diffractometry. In some embodiments, the gentisate salt and/or co-crystal further has at least one peak at diffraction angle 2θ(°) of 7.1±0.5, 8.7±0.5, and/or 26.7±0.5 as measured by X-ray powder diffractometry. In some embodiments, the gentisate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 12 as measured by X-ray powder diffractometry. In some embodiments, the gentisate salt and/or co-crystal has all of the peaks listed in Table 12 as measured by X-ray powder diffractometry.

TABLE 12

XRPD peak list for the gentisate salt and/or co-crystal of sepiapterin

| 2θ (°) | Intensity |
|---|---|
| 5.7 | 17.29 |
| 7.1 | 100.00 |
| 8.7 | 42.69 |
| 10.4 | 3.94 |
| 11.3 | 11.69 |
| 12.1 | 4.13 |
| 14.3 | 21.10 |
| 16.0 | 6.46 |
| 16.4 | 5.94 |
| 17.0 | 5.85 |
| 17.6 | 7.93 |
| 19.1 | 8.27 |
| 20.20 | 3.47 |
| 20.7 | 2.90 |
| 21.5 | 3.37 |
| 23.6 | 2.69 |
| 24.4 | 4.50 |
| 26.7 | 52.20 |
| 27.1 | 35.49 |
| 28.2 | 8.74 |
| 28.9 | 4.31 |
| 29.9 | 2.62 |
| 31.4 | 2.99 |
| 34.4 | 1.28 |
| 35.8 | 3.54 |
| 37.6 | 0.57 |

In some embodiments, the pharmaceutically acceptable salt and/or co-crystal of sepiapterin is a glycolate salt and/or co-crystal. In some embodiments, the glycolate salt and/or co-crystal has an endothermic onset at about 79° C. (e.g., from 77° C. to 81° C., such as 78° C. to 80° C.), 90° C. (e.g., from 88° C. to 92° C., such as 89° C. to 91° C.), 132° C. (e.g., from 130° C. to 134° C., such as 131° C. to 133° C.), and/or 152° C. (e.g., from 150° C. to 154° C., such as 151° C. to 153° C.) in differential scanning calorimetry (DSC) profile. In some embodiments, the glycolate salt and/or co-crystal has a loss of weight from 31° C. to 150° C. of less than 21% (e.g., less than 15%, less than 10%, less than 5%, or less than 1%) as measured by thermal gravimetric analysis.

In some embodiments, the glycolate salt and/or co-crystal has at least one peak at diffraction angle 2θ(°) of 7.6±0.5 as measured by X-ray powder diffractometry. In some embodiments, the glycolate salt and/or co-crystal further has at least one peak at diffraction angle 2θ(°) of 7.6±0.5, 10.7±0.5, and/or 24.0±0.5 as measured by X-ray powder diffractometry. In some embodiments, the glycolate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 13 as measured by X-ray powder diffractometry. In some embodiments, the glycolate salt and/or co-crystal has all of the peaks listed in Table 13 as measured by X-ray powder diffractometry.

TABLE 13

| XRPD peak list for the glycolate salt and/or co-crystal of sepiapterin | |
|---|---|
| 2θ (°) | Intensity |
| 4.8 | 6.23 |
| 7.6 | 100.00 |
| 10.3 | 68.06 |
| 10.7 | 70.69 |
| 15.3 | 36.51 |
| 18.2 | 24.25 |
| 18.7 | 27.26 |
| 19.9 | 2.66 |
| 21.2 | 17.11 |
| 24.0 | 96.62 |
| 24.4 | 18.44 |
| 28.8 | 47.57 |
| 30.3 | 7.43 |
| 32.5 | 4.42 |
| 33.3 | 7.49 |
| 34.3 | 5.21 |
| 36.3 | 7.37 |

In some embodiments, the acetate salt and/or co-crystal has at least one peak at diffraction angle 2θ(°) of 6.2±0.5 as measured by X-ray powder diffractometry. In some embodiments, the acetate salt and/or co-crystal further has at least one peak at diffraction angle 2θ(°) of 6.2±0.5, 12.0±0.5, and/or 18.1±0.5 as measured by X-ray powder diffractometry. In some embodiments, the acetate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 14 as measured by X-ray powder diffractometry. In some embodiments, the acetate salt and/or co-crystal has all of the peaks listed in Table 14 as measured by X-ray powder diffractometry.

TABLE 14

| XRPD peak list for the acetate salt and/or co-crystal of sepiapterin | |
|---|---|
| 2θ (°) | Intensity |
| 6.2 | 100.00 |
| 10.2 | 23.29 |
| 12.0 | 71.59 |
| 18.1 | 31.27 |
| 21.1 | 20.29 |
| 24.2 | 14.92 |
| 25.2 | 23.03 |
| 27.3 | 13.30 |
| 29.1 | 12.95 |

In another aspect, the invention features a composition (e.g., an solid composition) including any of the foregoing pharmaceutically acceptable salts and/or co-crystals and a pharmaceutically acceptable excipient. In some embodiments, the composition is stable at room temperature for at least 6 months. For example, the level of sepiapterin, or salt and/or co-crystal thereof, in the composition decreases by less than 5% (e.g., less than 4%, less than 3%, less than 2%, less than 1%) when the composition is stored at room temperature for 6 months and/or the level of lactoylpterin in the composition increases by less than 5% (e.g., less than 4%, less than 3%, less than 2%, or less than 1%) when the composition is stored at room temperature for 6 months. In some embodiments, the pharmaceutically acceptable salt and/or co-crystal contains less than 10% by weight (e.g., less than 5%, or less than 1%) of amorphous compound. In some embodiments, the pharmaceutically acceptable salt and/or co-crystal is substantially free of amorphous compound.

In some embodiments of any of the foregoing compositions, the composition includes an antioxidant (e.g., ascorbic acid), wherein the ratio of the pharmaceutically acceptable salt and/or co-crystal of sepiapterin to antioxidant is greater than 4:1 (e.g., greater than 5:1, greater than 6:1, greater than 7:1, greater than 8:1, greater than 9:1, greater than 10:1, greater than 15:1, or greater than 20:1) by weight (e.g., the weight of the salt and/or co-crystal to antioxidant).

In some embodiments of any of the foregoing compositions, the composition includes an antioxidant, wherein the pharmaceutical composition includes more pharmaceutically acceptable salt of sepiapterin than antioxidant by weight. For example, in some embodiments, the pharmaceutically acceptable salt and/or co-crystal of sepiapterin and antioxidant (e.g., ascorbic acid) are present in a ratio of at least 1:1 (e.g., 2:1, 3:1, 4:1, 5:1, 6:1, 7:1, 8:1, 9:1, or 10:1) by weight.

In some embodiments of any of the foregoing compositions, the composition includes an antioxidant, wherein the composition includes less than 10% (e.g., less than 9%, less than 8%, less than 7%, less than 6%, less than 5%, less than 4%, less than 3%, less than 2%, or less than 1%) antioxidant (e.g., ascorbic acid) by total weight. In some embodiments, the pharmaceutical composition is substantially free of antioxidant.

In some embodiments of any of the foregoing compositions, the composition includes less than 10% (e.g., less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, or less than 0.2%) lactoylpterin by total weight. In some embodiments, the pharmaceutical composition includes less than 1.3% lactoylpterin. In some embodiments, the pharmaceutical composition further includes an antioxidant (e.g., ascorbic acid). In other embodiments, the pharmaceutical composition does not include an antioxidant.

In some embodiments of any of the foregoing compositions, the composition is formulated for use in a suspension.

In some embodiments of any of the foregoing pharmaceutical compositions, the antioxidant is 4-chloro-2,6-di-tert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine mesylate, dodecyl gallate, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, tocopheryl acetate, vitamin A, vitamin B6, vitamin B12, or vitamin E, or a combination thereof. In some embodiments of any of the foregoing pharmaceutical compositions, the antioxidant is ascorbic acid, tocopherol, retinol, ascorbyl palmitate, N-acetyl cysteine, glutathione, butylatedhydroxytoluene, and/or butylatedhydroxyanisole.

In some embodiments of any of the foregoing compositions, the pharmaceutical composition includes about 20-95% (e.g., about 20%, about 21%, about 22%, about 23%, about 24%, about 25%, about 26%, about 27%, about 28%, about 29%, about 30%, about 40%, about 50%, about 60%, about 70%, about 80%, about 90%, about 95% or about 20-30%, about 25-45%, about 40-60%, about 50-75%, about 70-90%, about 85-95%) sepiapterin or the pharmaceutically acceptable salt and/or co-crystal thereof by total weight.

In some embodiments of any of the foregoing compositions, the pharmaceutical composition further includes a dispersant (e.g., a carboxymethylcellulose or a pharmaceutically acceptable salt and/or co-crystal thereof such as croscarmellose sodium). In some embodiments of any of the foregoing compositions, the pharmaceutical composition includes 0.1-1.5% (e.g., 0.1-0.3%, 0.2-0.4%, 0.3-0.5%, 0.4-0.6%, 0.5-0.7%, 0.6-0.8%, 0.7-0.9%, 0.8-1%, 0.9-1.1%, 1-1.2%, 1.1-1.3%, 1.2-1.4%, or 1.3-1.5%) dispersant (e.g., croscarmellose sodium) by total weight.

In some embodiments of any of the foregoing compositions, the pharmaceutical compositing includes at least one anti-caking agent or bulking agent (e.g., a bulking agent and an anti-caking agent). In some embodiments, the at least one anti-caking agent or bulking agent is colloidal silicon dioxide or microcrystalline cellulose. In some embodiments, the pharmaceutical composition includes 60-80% (e.g., about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%) anti-caking agent and/or bulking agent by total weight. In some embodiments of any of the foregoing compositions, the pharmaceutical composition includes both colloidal silicon dioxide and microcrystalline cellulose. In some embodiments of any of the foregoing compositions, the pharmaceutical composition includes 60-65% (about 60%, about 61%, about 62%, about 63%, about 64%, or about 65%) microcrystalline cellulose by total weight and 2-15% (e.g., about 2%, about 3%, about 4%, about 5%, about 6%, about 7%, about 8%, about 9%, about 10%, about 11%, about 12%, about 13%, about 14%, or about 15%) colloidal silicon dioxide by total weight.

In some embodiments of any of the foregoing compositions, the sepiapterin is formulated in particles less than 200 μm (e.g., less than 180 μm, less than 160 μm, less than 140 μm, less than 120 μm, less than 100 μm, or less than 80 μm) in size.

In some embodiments of any of the foregoing compositions, the pharmaceutical composition is formulated as particles (e.g., particles for use in a suspension). In some embodiments, the particles are less than 200 μm (e.g., less than 180 μm, less than 160 μm, less than 140 μm, less than 120 μm, less than 100 μm, or less than 80 μm) in size.

In some embodiments of any of the foregoing compositions, the pharmaceutical composition includes less than 50% (e.g., less than 40%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, or less than 0.2%) of lactoylpterin by weight of the combined amount of sepiapterin or salt and lactoylpterin. In some embodiments, the pharmaceutical composition includes less than 1.3% lactoylpterin.

In some embodiments of any of the foregoing compositions, the pharmaceutical composition further includes a dosing vehicle (e.g., dosing vehicle with a viscosity of about 50-1750 centipoise).

In some embodiments of any of the foregoing compositions, the pharmaceutical composition upon administration to a subject, results in greater plasma or liver cell levels (e.g., at least 1.1 times, at least 1.2 times, at least 1.3 times, at least 1.4 times, at least 1.5 times, at least 2 times, at least 3 times, or at least 4 times) of tetrahydrobiopterin (e.g., as measured by Tmax, Cmax, AUC, or concentration in the plasma at 15 minutes after administration) compared to that resulting from administration of a pharmaceutical composition including an equivalent dose of tetrahydrobiopterin.

In some embodiments of any of the foregoing compositions, the pharmaceutical composition, upon administration to a subject, results greater plasma or liver cell levels (e.g., at least 1.1 times, at least 1.2 times, at least 1.3 times, at least 1.4 times, at least 1.5 times, at least 2 times, at least 3 times, or at least 4 times) of tetrahydrobiopterin (e.g., as measured by Tmax, Cmax, AUC, or concentration in the plasma at 15 minutes after administration) compared to that resulting from administration of a pharmaceutical composition including an equivalent dose of sepiapterin or a pharmaceutically acceptable salt thereof and more than 10% antioxidant.

In an aspect, the invention features a method of producing a pharmaceutical composition including a pharmaceutically acceptable salt and/or co-crystal of sepiapterin. This method includes: a) mixing microcrystalline cellulose and colloidal silicon dioxide; b) adding the pharmaceutically acceptable salt and/or co-crystal of sepiapterin, a dispersant, and an antioxidant to the mixture of step a; and c) mixing the microcrystalline cellulose, colloidal silicon dioxide, pharmaceutically acceptable salt and/or co-crystal of sepiapterin, dispersant, and antioxidant, thereby producing a pharmaceutical composition including a pharmaceutically acceptable salt and/or co-crystal of sepiapterin.

In some embodiments, the mixture of microcrystalline cellulose and colloidal silicon dioxide is passed through a filter with pores of less than 200 μm (e.g., less than 180 μm, less than 160 am, less than 140 μm, less than 120 μm, less than 100 μm, or less than 80 μm) prior to step b.

In some embodiments, the mixture of microcrystalline cellulose, colloidal silicon dioxide, sepiapterin, dispersant, and antioxidant is passed through a filter with pores of less than 200 μm (e.g., less than 180 μm, less than 160 μm, less than 140 μm, less than 120 μm, less than 100 am, or less than 80 am).

In some embodiments of any of the foregoing compositions, the percentages by weight are measured for the dry composition (e.g., prior to suspension in a liquid such as water).

In some embodiments of any of the foregoing methods, the antioxidant is ascorbic acid. In some embodiments of any of the foregoing methods, the dispersant is croscarmellose sodium.

In an aspect, the invention features a method for treating a tetrahydrobiopterin-related disorder (e.g., phenylketonuria or a tetrahydrobiopterin deficiency) in a subject in need thereof, the method including administering an effective amount of any of the foregoing pharmaceutically acceptable salts and/or co-crystals or pharmaceutical compositions.

In an aspect, the invention features a method of increasing tetrahydrobiopterin levels in a subject in need thereof, the method including administering to the subject an effective amount of any of the foregoing pharmaceutically acceptable salts and/or co-crystals or pharmaceutical compositions.

In an aspect, the invention features a method of decreasing phenylalanine levels in a subject in need thereof, the method including administering to the subject an effective amount of any of the foregoing pharmaceutically acceptable salts and/or co-crystals or pharmaceutical compositions.

In an aspect, the invention features, a method of increasing the activity of phenylalanine hydroxylase in a subject, the method including administering to the subject an effective amount of any of the foregoing pharmaceutically acceptable salts and/or co-crystals or pharmaceutical compositions.

In an aspect, the invention features a method of treating phenylketonuria in a subject in need thereof, the method including administering to the subject an effective amount of any of the foregoing pharmaceutically acceptable salts and/or co-crystals or pharmaceutical compositions.

In an aspect, the invention features a method of treating gastroparesis in a subject in need thereof, the method including administering to the subject an effective amount of any of the foregoing pharmaceutically acceptable salts and/or co-crystals or pharmaceutical compositions.

In an aspect, the invention features a method of increasing serotonin levels in a subject in need thereof, the method including administering to the subject an effective amount of any of the foregoing pharmaceutically acceptable salts and/or co-crystals or pharmaceutical compositions.

In an aspect, the invention features a method of increasing the activity of tryptophan hydroxylase in a subject, the method including administering to the subject an effective amount of any of the foregoing pharmaceutically acceptable salts and/or co-crystals or pharmaceutical compositions.

In an aspect, the invention features a method of increasing dopamine levels in a subject in need thereof, the method including administering to the subject an effective amount of any of the foregoing pharmaceutically acceptable salts and/or co-crystals or pharmaceutical compositions.

In an aspect, the invention features a method of increasing the activity of tyrosine hydroxylase in a subject, the method including administering to the subject an effective amount of any of the foregoing pharmaceutically acceptable salts and/or co-crystals or pharmaceutical compositions.

In an aspect, the invention features a method of increasing the activity of nitric oxide synthases in a subject, the method including administering to the subject an effective amount of any of the foregoing pharmaceutically acceptable salts and/or co-crystals or pharmaceutical compositions.

In an aspect, the invention features a method of increasing the activity of alkylglycerol monooxygenase in a subject, the method including administering to the subject an effective amount of any of the foregoing pharmaceutically acceptable salts and/or co-crystals or pharmaceutical compositions.

In one aspect, the invention features a method of increasing the level of homovanillic acid and/or 5-hydroxyindoleacetic acid in a subject, the method comprising administering an effective amount of any of the foregoing pharmaceutically acceptable salts and/or co-crystals or pharmaceutical compositions. In one embodiment, the pharmaceutically acceptable salt and/or co-crystal is a methanesulfonate salt and/or co-crystal, a nicotinate salt and/or co-crystal, a toluenesulfonate salt and/or co-crystal, a benzenesulfonate salt and/or co-crystal, a sulfate salt and/or co-crystal, a phosphate salt and/or co-crystal, a malonate salt and/or co-crystal, a tartrate salt and/or co-crystal, a fumarate salt and/or co-crystal, a gentisate salt and/or co-crystal, or a glycolate salt and/or co-crystal. In some embodiments, the level of homovanillic acid and/or 5-hydroxyindoleacetic acid in the cerebrospinal fluid (CSF) of the subject is increased. In some embodiments, the level of homovanillic acid and/or 5-hydroxyindoleacetic acid in the subject (e.g., in the CSF of the subject) is increased at least 5% compared to the level prior to administration (e.g., the level is increased at least 10%, at least 20%, at least 30%, at least 40%, at least 50%, at least 60%, at least 70%, at least 80%, at least 90%, at least 100%, at least 150%, at least 200%, at least 250%, at least 300% compared to the level prior to administration).

In some embodiments, prior to administration of the pharmaceutically acceptable salt and/or co-crystal or pharmaceutical composition, the subject has levels of homovanillic acid and/or 5-hydroxyindoleacetic acid that are less than 50% (e.g., less than 40%, less than 30%) of the levels an average subject, (e.g., the subject has CSF levels of homovanillic acid of less than 15 ng/mL and/or has CSF levels of 5-hydroxyindoleacetic acid of less than 5 ng/mL). In some embodiments, the subject has not been diagnosed with a BH4-related disorder. In some embodiments, the subject does not have symptoms of a BH4-related disorder. In some embodiments, after administration of the pharmaceutically acceptable salt and/or co-crystal or pharmaceutical composition, the levels of homovanillic acid and/or 5-hydroxyindoleacetic in the subject are greater than 50% of the levels of an average subject, (e.g., the subject has CSF levels of homovanillic acid of greater than 15 ng/mL and/or has CSF levels of 5-hydroxyindoleacetic acid of greater than 5 ng/mL).

In some embodiments of any of the foregoing methods, the effective amount of any of the foregoing pharmaceutically acceptable salts and/or co-crystals or pharmaceutical compositions includes an amount sufficient to increase the level of tetrahydrobiopterin in the plasma of the subject 1 hour after administration by at least a factor of two (e.g., at least a factor of 3, 4, 5, 6, 7, 9, or 10) compared to the level of tetrahydrobiopterin prior to administration.

In some embodiments of any of the foregoing methods, the effective amount of any of the foregoing pharmaceutically acceptable salts and/or co-crystals or pharmaceutical compositions includes an amount sufficient to increase the level of tetrahydrobiopterin in the CSF and/or brain of the subject 1 hour after administration by at least a factor of two (e.g., at least a factor of 3, 4, 5, 6, 7, 9, or 10) compared to the level of tetrahydrobiopterin prior to administration.

In some embodiments of any of the foregoing methods, the subject is human. In some embodiments of any of the foregoing methods, the method includes combining any of the foregoing pharmaceutically acceptable salts or pharmaceutical compositions with a dosing vehicle prior to administration.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

The term "anti-caking agent" refers to an additive added to powdered or granulated pharmaceutical formulations to prevent the formation of lumps. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane.

The term "antioxidant" refers to agents that can minimize the oxidative degradation of an active pharmaceutical ingredient. Examples of antioxidants include ascorbic acid, tocopherol, retinol, ascorbyl palmitate, N-acetyl cysteine, glutathione, ethylenediaminetetraacetic acid, sodium bisulfite, sodium metabisulfite, thiourea, butylatedhydroxytoluene, butylatedhydroxyanisole, vitamin E, 4-chloro-2,6-di-tert-butylphenol, alkylated diphenylamines, ascorbyl myristate, ascorbyl stearate, beta-carotene, citric acid, cysteine, D-alpha-tocopheryl polyethylene glycol 1000 succinate, deferoxamine methanesulfonate, dodecyl gallate, ethylparaben, folic acid, fumaric acid, gallic acid, lecithin, malic acid, methylparaben, monothioglycerol, nordihydroguaiaretic acid, octyl gallate, p-phenylenediamine, potassium ascorbate, potassium metabisulfite, potassium sorbate, propionic acid, propyl gallate, sorbic acid, sodium ascorbate, sodium hydrosulfite, sodium isoascorbate, sodium sulfite, sodium thiosulfate, tartaric acid, tert-butylhydroquinone, tocopheryl acetate, vitamin A, vitamin B6, and vitamin B12.

As used herein, the term "BH4-related disorder" or "tetrahydrobiopterin-related disorder," refers to any disease or disorder that may derive a therapeutic benefit from modulation (e.g., increase) of the level of BH4, e.g., phenylketonuria.

By "determining the level of a compound" is meant the detection of a compound, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure compound levels generally include, but are not limited to, liquid chromatography (LC)-mass spectrometry.

The term "dispersant" refers to an agent used in pharmaceutical formulations, which causes particles in a formulation to separate, e.g., release their medicinal substances on contact with moisture. Examples include crosslinked polyvinylpyrrolidone, carboxymethylcellulose (e.g., croscarmellose salt, e.g., croscarmellose sodium), starch (e.g., sodium starch glycolate), or alginic acid.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. A therapeutically effective amount also encompasses an amount sufficient to confer benefit, e.g., clinical benefit.

By "increasing the activity of" an enzyme, is meant increasing the level of an activity related to the enzyme, e.g., phenylalanine hydroxylase, or a related downstream effect. A non-limiting example of increasing an activity of an enzyme includes increasing the activity of phenylalanine hydroxylase resulting in a decrease in the level of phenylalanine. The activity level of an enzyme may be measured using any method known in the art.

By "level" is meant a level of a compound, as compared to a reference. The reference can be any useful reference, as defined herein. By a "decreased level" or an "increased level" of a compound is meant a decrease or increase in compound level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a compound may be expressed in mass/vol (e.g., g/dL, mg/mL, μg/mL, ng/mL) or percentage relative to total compound in a sample.

The term "pharmaceutical composition," as used herein, represents a composition containing a compound described herein formulated with a pharmaceutically acceptable excipient. A pharmaceutical composition may be one manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gel cap, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

As used herein, the term "pharmaceutically acceptable salt" means any pharmaceutically acceptable salt of sepiapterin. Pharmaceutically acceptable salts include ion pairs of sepiapterin in the solid state and/or in solution. A pharmaceutically acceptable co-crystal includes freebase sepiapterin and an acid in a solid state. Mixture of the salt form and co-crystal form may be present in the same composition. For example, pharmaceutically acceptable salts of sepiapterin include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: in Remington (Remington: The Science and Practice of Pharmacy, (22nd ed.) ed. L. V. Allen, Jr., 2013, Pharmaceutical Press, Philadelphia, PA). The salts can be prepared in situ during the final isolation and purification of the compounds described herein or separately by reacting a free base group with a suitable organic acid.

Sepiapterin may be prepared as pharmaceutically acceptable salts and/or co-crystals. These salts may be acid addition salts involving inorganic or organic acids. Suitable pharmaceutically acceptable acids and methods for preparation of the appropriate salts are well-known in the art.

By a "reference" is meant any useful reference used to compare compound levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified compound (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified compound, e.g., any described herein, within the normal reference range can also be used as a reference.

As used herein, the term "subject" or "patient" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results.

Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION

Figure 1:
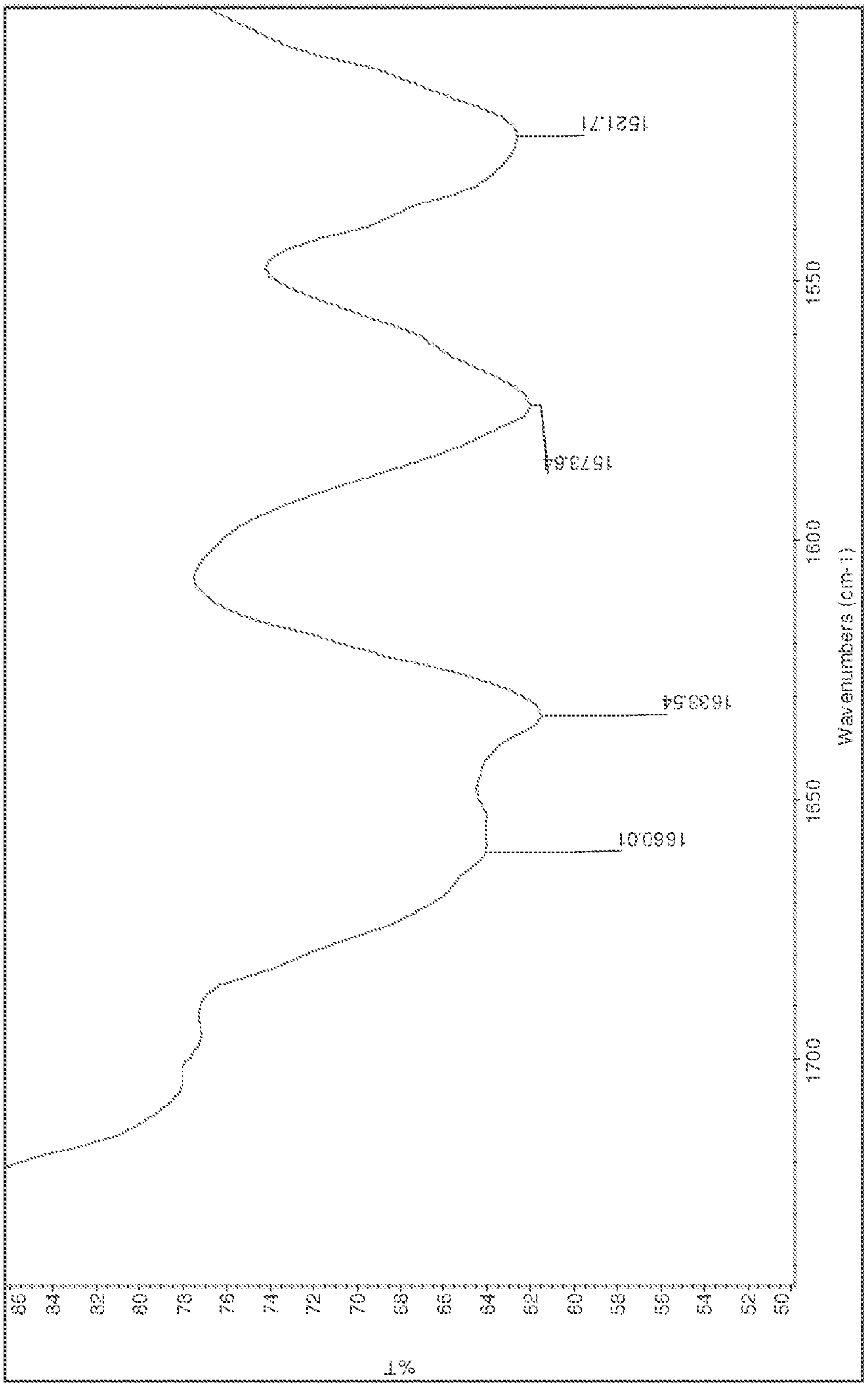
FIG. 1 is an IR spectrum of a free base of sepiapterin.

The present invention features pharmaceutically acceptable salts and/or co-crystals of sepiapterin, compositions thereof, and methods for the treatment of tetrahydrobiopterin-related disorders with such compositions. The present inventors have surprisingly found that some salts and/or co-crystals of sepiapterin have improved properties, e.g., improved stability, purity, exposure, and/or bioavailability.

Compounds

Sepiapterin

The pharmaceutical compositions of the invention comprise sepiapterin, or a pharmaceutically acceptable salt and/or co-crystal thereof. Sepiapterin has the structure:

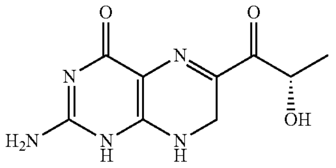

and

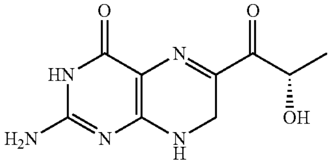

.

Sepiapterin

In some embodiments, a pharmaceutically acceptable salt and/or co-crystal of sepiapterin is present in a pharmaceutical composition of the invention in a crystalline form, as described herein.

In some embodiments, a pharmaceutical composition of the invention includes 20-30% of a pharmaceutically acceptable salt and/or co-crystal of sepiapterin by total weight, e.g., 20%, 22%, 25%, 27%, or 30%. In some embodiments, a pharmaceutical composition includes greater than 20% of a pharmaceutically acceptable salt and/or co-crystal of sepiapterin by total weight, e.g., greater than 25%, greater than 30%, greater than 40%, greater than 50%, greater than 60%, greater than 70%, greater than 80%, or greater than 90%.

Tetrahydrobiopterin

Sepiapterin, upon administration to a subject, is converted to tetrahydrobiopterin. Tetrahydrobiopterin has the structure:

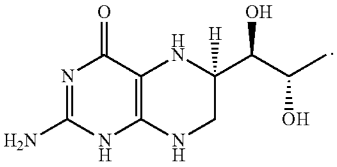

.

Tetrahydrobiopterin

Lactoylpterin

An impurity that may be present in sepiapterin preparations is lactoylpterin, which may result from oxidation of sepiapterin. Lactoylpterin has the structure:

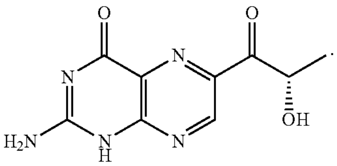

.

Lactoylpterin

Excipients

Antioxidants

Sepiapterin is prone to rapid oxidation when exposed to air. Accordingly, a pharmaceutical composition of the invention may include an antioxidant. The antioxidant may minimize the oxidative degradation of sepiapterin. Examples of antioxidants include, but are not limited to, 4-chloro-2,6-di-tert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine methanesulfonate, dodecyl gallate, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, tocopheryl acetate, vitamin A, vitamin B6, vitamin B12, or vitamin E. In some embodiments, a pharmaceutical composition of the invention includes ascorbic acid, tocopherol, retinol, ascorbyl palmitate, N-acetyl cysteine, glutathione, butylatedhydroxytoluene, and/or butylatedhydroxyanisole as antioxidant.

In some embodiments, the pharmaceutical composition includes less than 10% antioxidant by weight, e.g., less than 9%, less than 8%, less than 7%, less than 6%, less than 5%, less than 4%, less than 3%, less than 2%, or less than 1%. In some embodiments, the pharmaceutical composition includes 2-9% antioxidant by total weight, e.g., 2-4%, 3-5%, 4-6%, 5-7%, 6-8%, or 7-9%. In some embodiments, the pharmaceutical composition includes 5-100% of the USP maximum daily dose of the antioxidant, e.g., in some embodiments, the pharmaceutical composition includes 5%, 10%, 15%, 20%, 30%, 40%, 50%, 60%, 70%, 80%, 90%, or 100% of the USP maximum daily dose of the antioxidant. In some embodiments, the ratio of sepiapterin or pharmaceutically acceptable salt and/or co-crystal thereof to antioxidant is at least 1:1, e.g., 2:1, 3:1, 4:1, 5:1, 6:1, 7:1, 8:1, 9:1, or 10:1 wt/wt.

In some embodiments of any of the foregoing compositions, the composition includes an antioxidant (e.g., ascorbic acid), wherein the ratio of the pharmaceutically acceptable salt and/or co-crystal of sepiapterin to antioxidant is greater than 4:1 (e.g., greater than 5:1, greater than 6:1, greater than 7:1, greater than 8:1, greater than 9:1, greater than 10:1, greater than 15:1, or greater than 20:1) by weight (e.g., the weight of the salt to antioxidant).

As previous formulations of sepiapterin included as much as 50% antioxidant (e.g., ascorbic acid) or more, it is surprising that compositions including less than 10% antioxidant or even no antioxidant are effective at stabilizing pharmaceutically acceptable salts and/or co-crystals of sepiapterin.

Dispersants

In some embodiments, a pharmaceutical composition of the invention includes at least one dispersant. The dispersant may cause particles in the formulation to separate, e.g., release their medicinal substances on contact with moisture. Examples of dispersant include, but are not limited to, crosslinked polyvinylpyrrolidone, carboxymethylcellulose (e.g., croscarmellose salt, e.g., croscarmellose sodium), starch (e.g., sodium starch glycolate), or alginic acid. In some embodiments, the dispersant in the pharmaceutical composition is a carboxymethylcellulose such as a pharmaceutically acceptable salt of croscarmellose. In some embodiments, the pharmaceutical composition may include 0.1-1.5% dispersant by total weight, e.g., 0.1%, 0.5%, 1%, or 1.5%. In some embodiments, the pharmaceutical composition includes less than 1.5% dispersant, e.g., less than 1%, less than 0.5%, or less than 0.1%.

Anti-Caking Agents

Sepiapterin has been found to clump when added to aqueous solutions. Anti-caking agents are often added to pharmaceutical compositions to prevent the formation of lumps, e.g., in solutions. Accordingly, in some embodiments, the pharmaceutical compositions of the invention include at least one anti-caking agent. In some embodiments, the pharmaceutical compositions include at least two anti-caking agents. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane. In some embodiments, the at least one anti-caking agent is colloidal silicon dioxide or microcrystalline cellulose. In some embodiments, the pharmaceutical composition may include 65-75% anti-caking agent by total weight, e.g., 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight.

Dosing Vehicle

In some embodiments, a pharmaceutical composition of the invention is combined with a dosing vehicle prior to administration. In some embodiments of any of the foregoing compositions, the composition may be administered in a dosing vehicle with a viscosity of approximately 50-1750 centipoise (cP), e.g., to aid suspension and dosing of the pharmaceutical composition. One type of suspending agent that can be used is a combination of glycerin and sucrose in water (e.g., MEDISCA® oral mix with 2.5% glycerin and 27% sucrose in water). An appropriate quantity of composition can be added to the dosing vehicle mixture and agitated to suspend the composition just prior to administration.

Other suspending agents may also be used as a dosing vehicle. Exemplary suspending agents include agar, alginic acid, sodium carboxymethyl cellulose, carrageenan, dextrin, gelatin, guar gum, hydroxyethyl cellulose, hydroxypropyl cellulose, hypromellose, methyl cellulose, polyethylene glycol, povidone, tragacanth, xanthan gum, or other suspending agents known in the art.

Formulations

In some embodiments, the invention features a pharmaceutical composition including a pharmaceutically acceptable salt and/or co-crystal of sepiapterin, e.g., and less than 10% by total weight of an antioxidant, e.g., 9%, 7%, 5%, 3%, 1%, 0.5%, 0.25%, or 0.1%. The antioxidant may be ascorbic acid. In some embodiments, the ratio of the pharmaceutically acceptable salt and/or co-crystal of sepiapterin to the antioxidant is 1:1, e.g., 2:1, 5:1, 7:1, or 10:1 wt/wt. In some embodiments of any of the foregoing compositions, the composition includes an antioxidant (e.g., ascorbic acid), wherein the ratio of the pharmaceutically acceptable salt and/or co-crystal of sepiapterin to antioxidant is greater than 4:1 (e.g., greater than 5:1, greater than 6:1, greater than 7:1, greater than 8:1, greater than 9:1, greater than 10:1, greater than 15:1, or greater than 20:1) by weight (e.g., the weight of the salt to antioxidant). A pharmaceutical composition may include 20-30% a pharmaceutically acceptable salt and/or co-crystal of sepiapterin by total weight, e.g., 20%, 22%, 25%, 27%, or 30%. A pharmaceutical composition can further include a dispersant, e.g., croscarmellose sodium. The pharmaceutical composition may include 0.1-1.5% dispersant by total weight, e.g., 0.1%, 0.5%, 1%, or 1.5%. In some embodiments, a pharmaceutical formulation includes at least one anti-caking agent, e.g., colloidal silicon dioxide or microcrystalline cellulose. A pharmaceutical composition may include 65-75% anti-caking agent by total weight, e.g., 65%, 67%, 70%, 73%, or 75%. In some embodiments, a pharmaceutical composition includes both colloidal silicon dioxide and microcrystalline cellulose. In some embodiments, a pharmaceutical composition includes 60-65% microcrystalline cellulose by total weight and 5-7% colloidal silicon dioxide by total weight. In some embodiments, the pharmaceutically acceptable salt and/or co-crystal of sepiapterin is formulated as particles less than 140 μm in size, e.g., 120 μm, 110 μm, 100 μm, 90 μm, 80 μm, 70 μm, 60 μm, 50 μm, 40 μm, 30 μm, 20 μm, 10 μm, or 5 μm. In some embodiments, a pharmaceutical composition includes less than 1.3%, e.g., less than 1%, of an impurity such as lactoylpterin, e.g., the composition includes less than 0.9%, less than 0.8%, less than 0.7%, less than 0.6%, less than 0.5%, less than 0.4%, less than 0.3%, or less than 0.2%.

A pharmaceutically acceptable salt and/or co-crystal of sepiapterin may serve as a useful therapeutic for diseases associated with low intracellular BH4 levels or with dysfunction of various BH4 dependent metabolic pathways including, but not limited to, primary tetrahydrobiopterin deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, and hypoglycemia. Thus, the various forms of sepiapterin in accordance with the present invention can be administered to a patient in an effective amount to obtain a treatment or amelioration of the disease, disorder or condition.

In some embodiments, the salt and/or co-crystal is a salt and/or co-crystal of sepiapterin with sulfuric acid, p-toluenesulfonic acid, methanesulfonic acid, benzenesulfonic acid, malonic acid, tartaric acid (e.g., L-tartaric acid), phosphoric acid, gentisic acid, fumaric acid, glycolic acid, acetic acid, or nicotinic acid.

In some embodiments, the pharmaceutical composition comprises a crystalline salt and/or co-crystal of sepiapterin. The crystalline salt and/or co-crystal of sepiapterin can occur as an anhydrate (e.g., without having any bound water or solvent or hydration or solvation) or as a hydrate, a partial hydrate (e.g., hemihydrate, sesquihydrate), as a dihydrate, a trihydrate, wherein the crystalline form binds a water of hydration or a solvent molecule associated with the crystalline form of sepiapterin or salt and/or co-crystal thereof. In an embodiment, crystalline salt and/or co-crystal of sepiapterin occurs as a monohydrate or as a hemihydrate.

The present invention provides a pharmaceutical composition including a pharmaceutically acceptable carrier and an effective amount, e.g., a therapeutically effective amount, including a prophylactically effective amount, of a pharmaceutically acceptable salt and/or co-crystal of sepiapterin.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; a pharmaceutically acceptable salt and/or co-crystal of sepiapterin can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

Dosage

A pharmaceutically acceptable salt of sepiapterin can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically, the dosages range from about 2.5 to about 150 mg/kg body weight of the patient being treated/day. For example, in embodiments, a pharmaceutically acceptable salt of sepiapterin, may be administered from about 20 mg/kg to about 200 mg/kg, from about 40 mg/kg to about 150 mg/kg, from about 60 mg/kg to about 120 mg/kg, from about 80 mg/kg to about 100 mg/kg, from about 40 mg/kg to about 60 mg/kg, from about 2.5 mg/kg to about 20 mg/kg, from about 2.5 mg/kg to about 10 mg/kg, from about 2.5 mg/kg to about 5 mg/kg, of subject body weight per day, one or more times a day, to obtain the desired therapeutic effect.

In some embodiments, the dose is an amount sufficient to produce levels of BH4 in the CNS, e.g., as measured in the CSF and/or brain and/or sufficient to produce a therapeutic results, e.g., increased levels of serotonin or dopamine in the CNS. In some embodiments, the dose is an amount sufficient to increase levels of BH4 at least two times greater than the levels of BH4 prior to administration as measured in the plasma or an organ of the subject, e.g., the liver of the subject.

In some embodiments, a pharmaceutically acceptable salt and/or co-crystal of sepiapterin can be formulated into unit solid oral dosage forms such as particles. In these embodiments, each unit solid oral dosage form can comprise any suitable amount of a pharmaceutically acceptable salt and/or co-crystal of sepiapterin. For example, each solid oral dosage form can comprise about 2.5 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg.

Routes of Administration

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intra-arterial, intramuscular, intraperitoneal, intrathecal, rectal, and vaginal administration are merely exemplary and are in no way limiting.

A pharmaceutical composition may be a liquid formulation, such as in the form of a solution, suspension, or emulsion. Formulations suitable for oral administration can consist of (a) capsules, sachets, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for oral and/or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazopeak quaternary ammonium salts, and (3) mixtures thereof.

The parenteral formulations will typically contain from about 20 to about 30% by weight of sepiapterin or pharmaceutically acceptable salt and/or co-crystal thereof in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

A pharmaceutical composition may be an injectable formulation. The requirements for effective pharmaceutical carriers for injectable compositions are well known to those of ordinary skill in the art. See Remington: The Science and Practice of Pharmacy, (22nd ed.) ed. L. V. Allen, Jr., 2013, Pharmaceutical Press, Philadelphia, PA.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains sepiapterin and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

A pharmaceutical composition may be an aerosol formulation to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Additionally, a pharmaceutical composition may be a suppository. Formulations suitable for vaginal administration may be presented as pessaries, tampons, creams, gels, pastes, foams, or spray formulas containing, in addition to the active ingredient, such carriers as are known in the art to be appropriate.

Solid Dosage Form for Oral Administration

Formulations for oral use include particles containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, anti-adhesives (e.g., magnesium stearate, zinc stearate, stearic acid, silicas, hydrogenated vegetable oils, or talc), and anti-caking agents (e.g., colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions of the invention may include a coating adapted to protect the composition from unwanted chemical changes, (e.g., chemical degradation prior to the release of the active substances). The coating may be applied on the solid dosage form in a similar manner as that described in Remington: The Science and Practice of Pharmacy, (22nd ed.) ed. L. V. Allen, Jr., 2013, Pharmaceutical Press, Philadelphia, PA.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

Methods of Treatment

The present invention features pharmaceutical compositions, e.g., in an orally tolerable formula that contains a therapeutically effective amount of a pharmaceutically acceptable salt and/or co-crystal of sepiapterin, e.g., and less than 10% antioxidant. In some embodiments, the pharmaceutical composition is a granular formulation that is dispersed in a pharmaceutically acceptable carrier, for example the composition can be mixed into water and ingested by a patient (e.g., over the course of 5 to 10 minutes). Suitable formulations for use in the present invention are found in Remington: The Science and Practice of Pharmacy, (22nd ed.) ed. L. V. Allen, Jr., 2013, Pharmaceutical Press, Philadelphia, PA. Except insofar as any conventional carrier is incompatible with the active ingredient, its use in the pharmaceutical compositions is contemplated. Moreover, for animal (e.g., human) administration, it will be understood that preparations should meet sterility, pyrogenicity, general safety and purity standards as required by regulatory agencies.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, patients receive 2.5 mg/kg/day, 5 mg/kg/day 10 mg/kg/day 20 mg/kg/day, 40 mg/kg/day, 60 mg/kg/day, or 80 mg/kg/day of a pharmaceutically acceptable salt and/or co-crystal of sepiapterin. Patients may receive the pharmaceutical composition including sepiapterin once daily, twice daily or three times daily during treatment. In some embodiments, patients continue their other current medications for BH4-related disorder (e.g., L-dopa/carbidopa, 5HTP, melatonin, MAO inhibitors, and dopamine receptor agonists as prescribed) except for BH4 supplementation (if they are taking BH4). Patients may not be permitted to take any drugs known to inhibit folate synthesis (e.g., methotrexate, pemetrexed, or trimetrexate).

In some embodiments, patients taking BH4 therapy prior to study entry undergo a "washout" period during screening prior to administration of the pharmaceutical composition of the invention. Patients may be instructed to maintain a consistent diet, with respect to protein and phenylalanine (Phe) intake. Diet records may be reviewed by a qualified dietician. Total Phe concentrations for the 3-day period may be calculated by the dietician and recorded.

In some embodiments, patients who are taking BH4 discontinue administration of BH4 (i.e., BH4 washout). Blood samples for Phe concentrations may be obtained during the BH4 washout period at 7, 5, 3, and 1 day before the treatment with the pharmaceutical composition of the invention or until blood Phe levels are >360 μmol/L at any time point during BH4 washout. In some embodiments, pre-dose blood sample are tested for sepiapterin, Phe, BH4, and tyrosine (Tyr).

Methods of Producing Formulations

In some embodiments, a pharmaceutical composition of the invention may be produced by mixing sepiapterin or pharmaceutically acceptable salt and/or co-crystal thereof and an antioxidant with one or more excipients, e.g., a dispersant and one or more anti-caking agents. In some embodiments, each of the components of the composition are passed through a size exclusion filter (e.g., a filter having pores of 200 μm or less) prior to mixing. In some embodiments, the anti-caking agents are mixed together prior to the addition of the components (e.g., the sepiapterin, dispersant, and antioxidant).

In some embodiments, the pharmaceutical composition is produced by:

(a) passing at least one anti-caking agent through a size exclusion filter (e.g., a filter having pores less than 200 μm);

(b) combining the sepiapterin, antioxidant, and optionally a dispersant with the at least one anti-caking agent (e.g., by mixing in a blender); and (c) passing the combination of step b through a size exclusion filter (e.g., a filter having pores less than 150 μm).

In some embodiments, the at least one anti-caking agent of step a includes more than one anti-caking agent (e.g., two anti-caking agents) that have been mixed together prior to be passed through the size exclusion filter.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. As such, the following examples are provided to teach various aspects of the present invention. These examples represent individual embodiments of the aspects of this invention and one skilled in the art will recognize that additional examples can be generated in order to equally teach the aspects of the present invention.

Example 1. Preparation of Salts of Sepiapterin

Salts and/or co-crystals of sepiapterin and hydrochloric acid, methanesulfonic acid, toluenesulfonic acid, benzenesulfonic acid, nicotinic acid, sulfuric acid, phosphoric acid, malonic acid, L-tartric acid, fumaric acid, gentisic acid, and glycolic acid were produced by slurrying the free base of sepiapterin and the acid in acetone/water (9/1, v/v) or methanol for 2-17 days.

Figure 2:
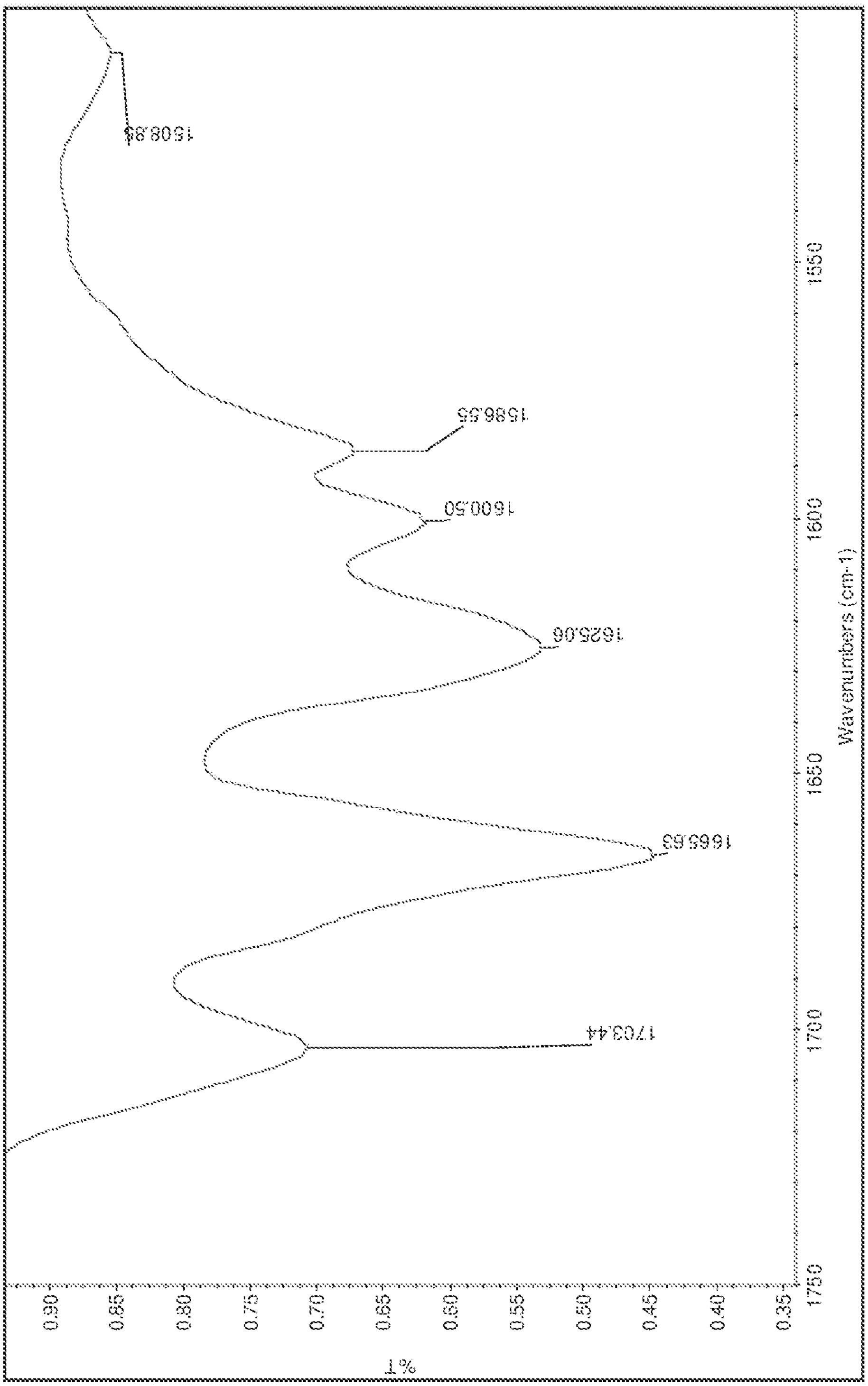
FIG. 2 is an IR spectrum of a hydrochloride salt and/or co-crystal of sepiapterin.
Figure 3:
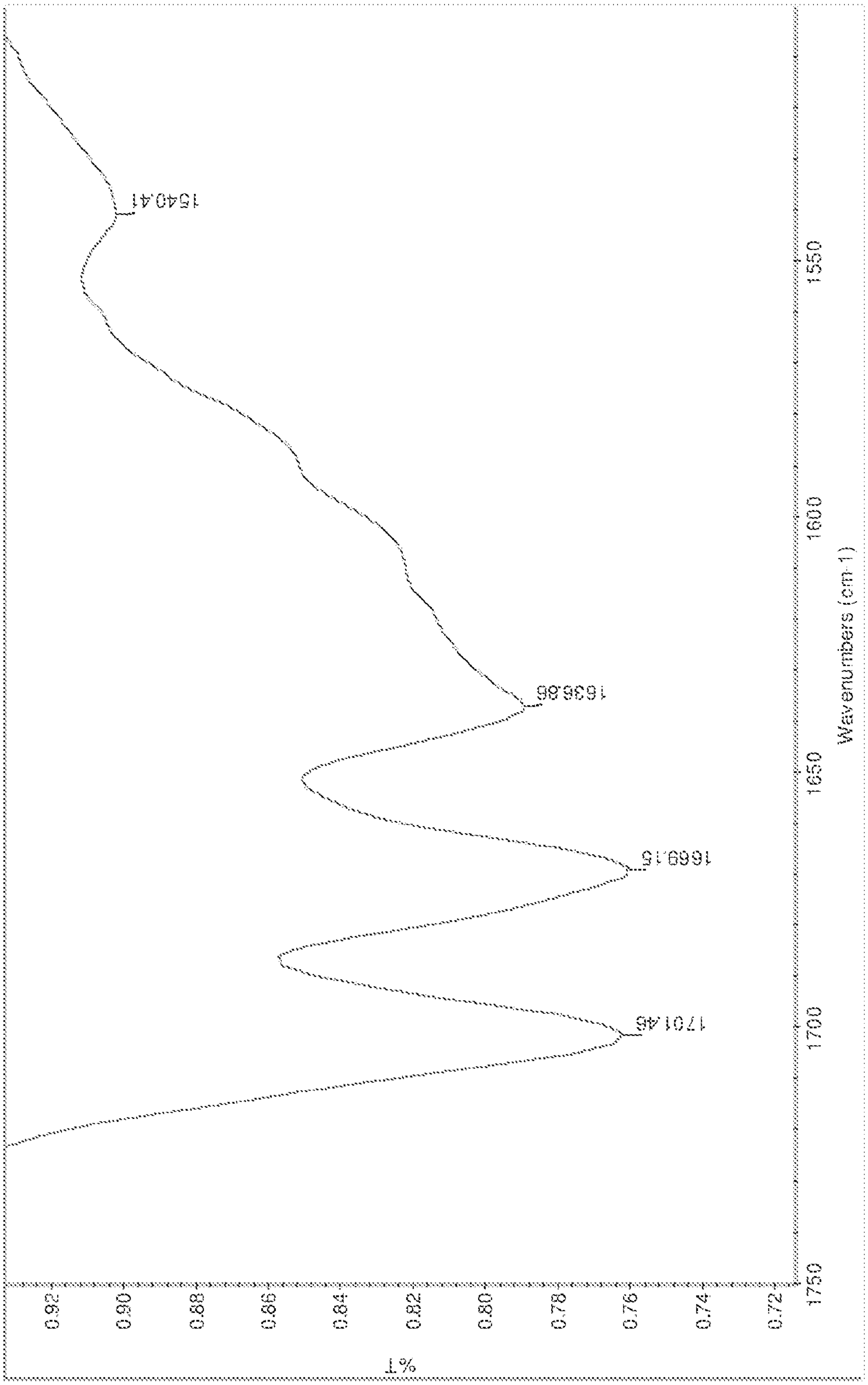
FIG. 3 is an IR spectrum of a methanesulfonate salt and/or co-crystal of sepiapterin.
Figure 4:
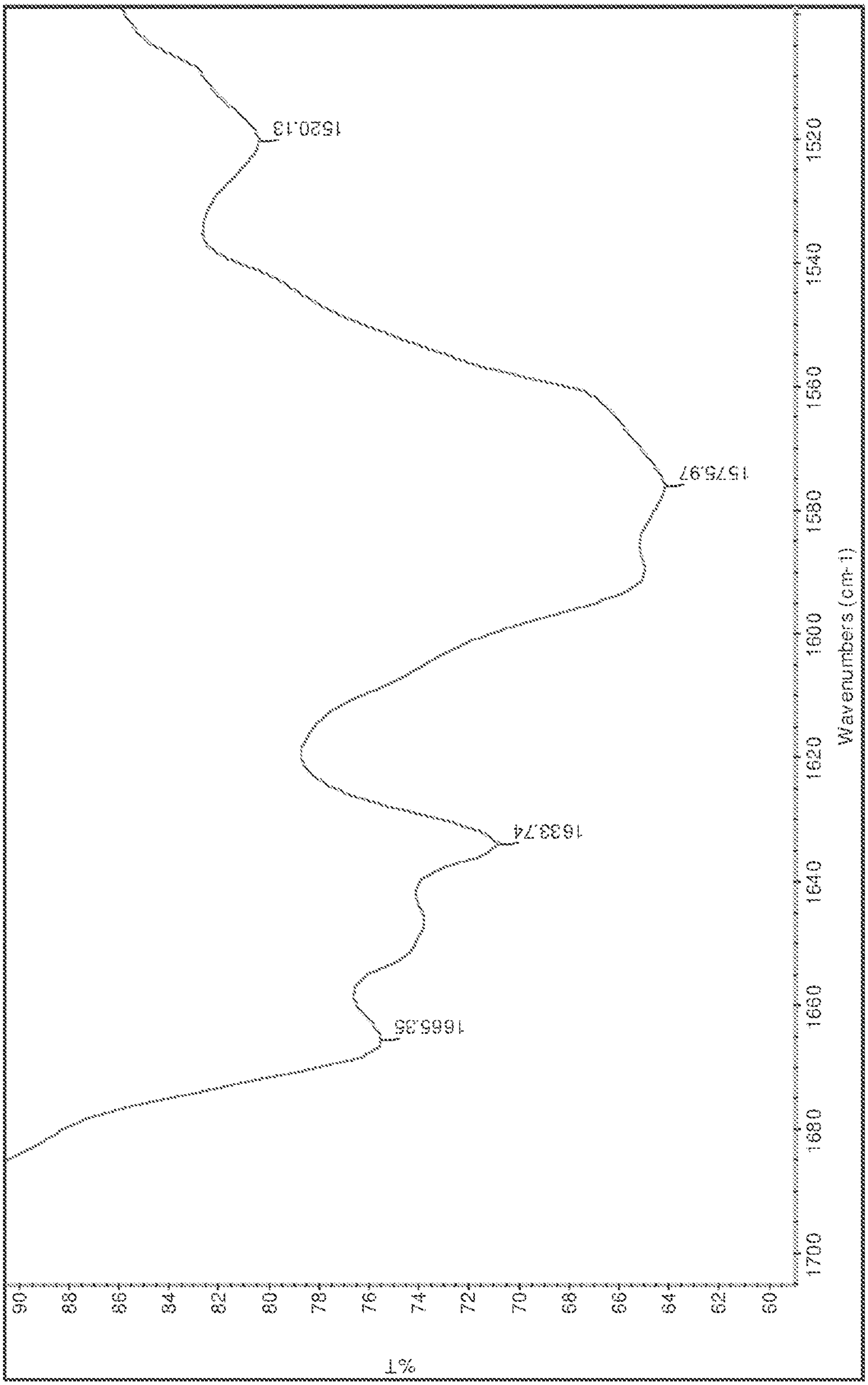
FIG. 4 is an IR spectrum of a nicotinate salt and/or co-crystal of sepiapterin.
Figure 5:
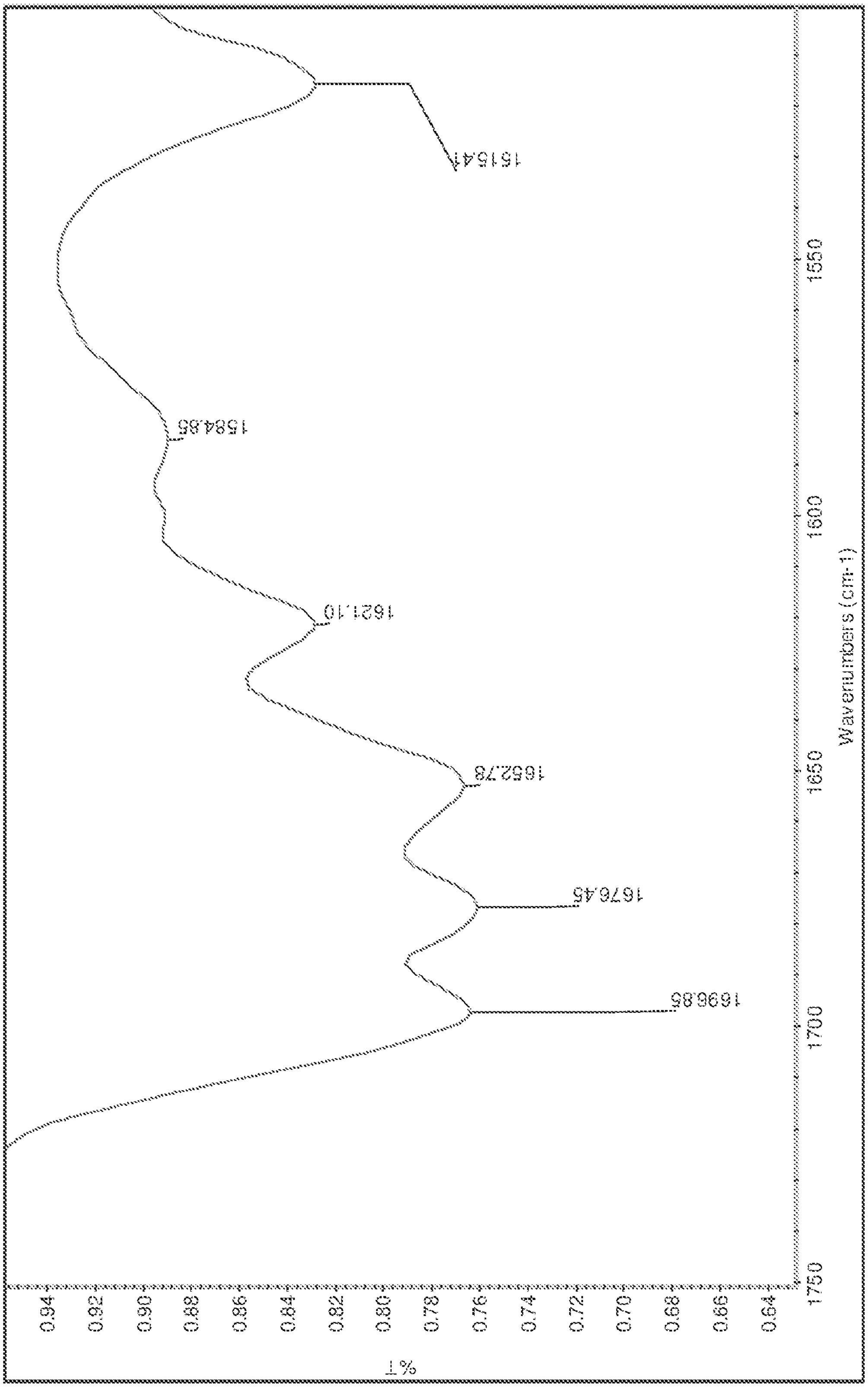
FIG. 5 is an IR spectrum of a toluenesulfonate salt and/or co-crystal of sepiapterin.
Figure 6:
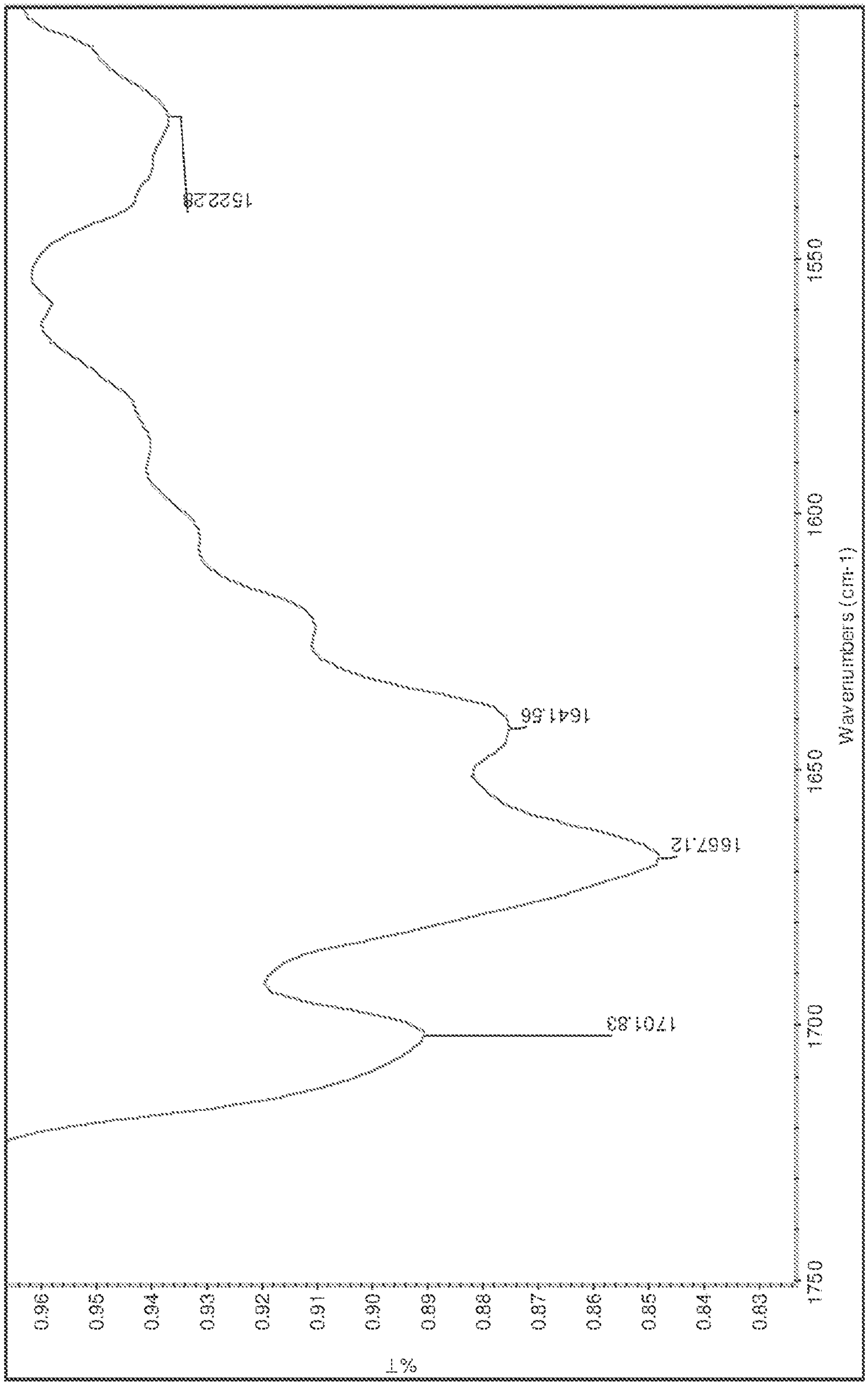
FIG. 6 is an IR spectrum of a benzenesulfonate salt and/or co-crystal of sepiapterin.
Figure 7:
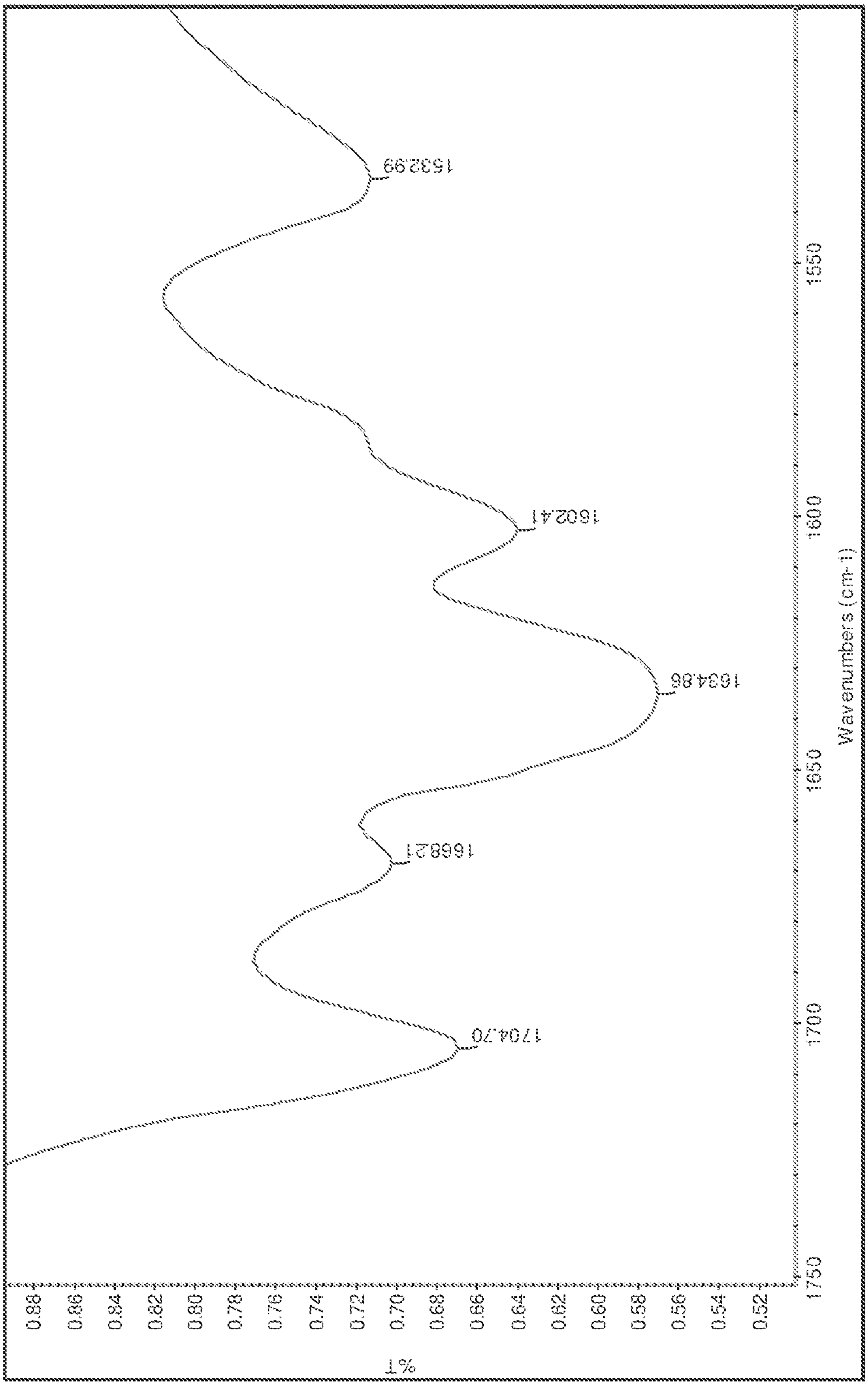
FIG. 7 is an IR spectrum of a sulfate salt and/or co-crystal of sepiapterin.
Figure 8:
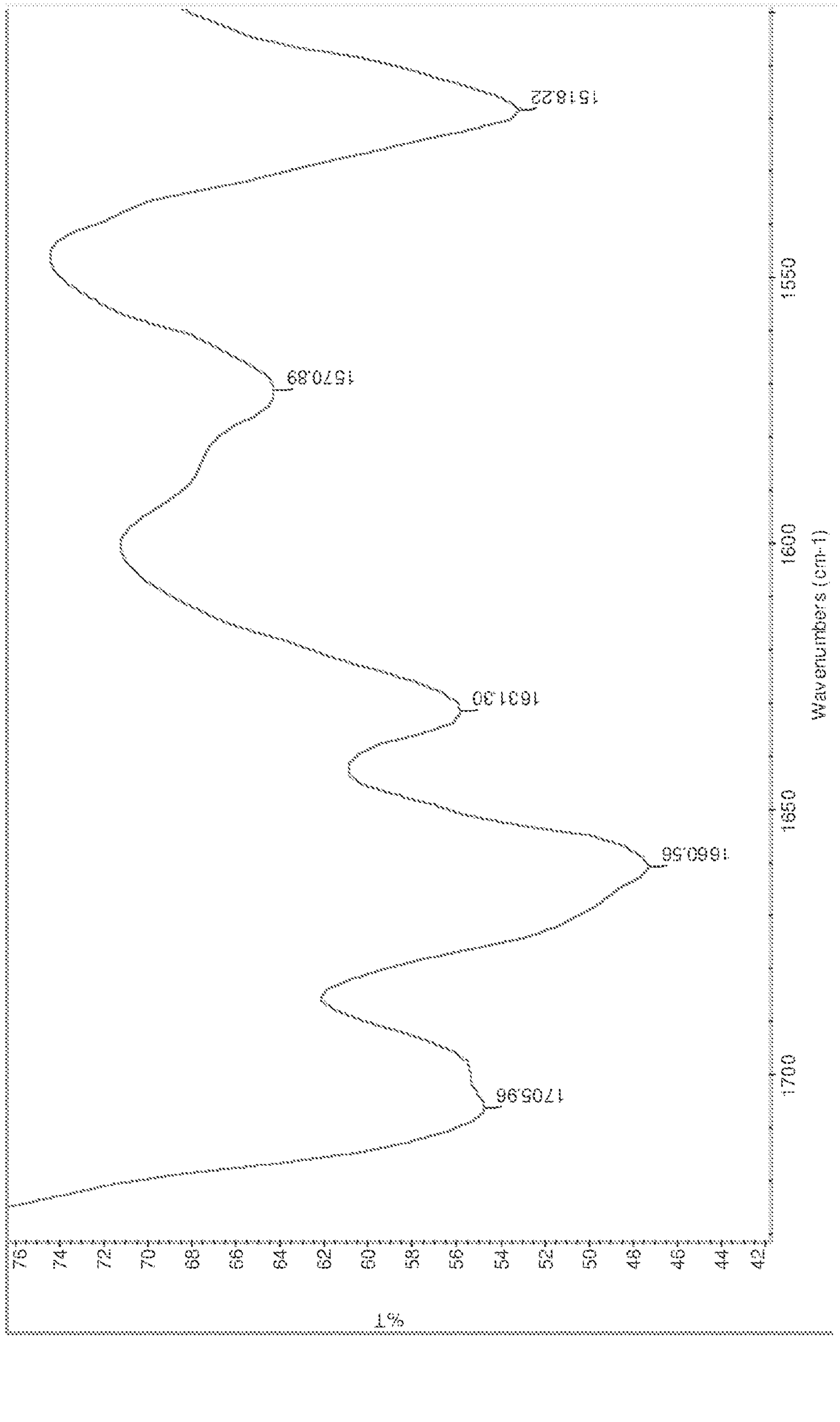
FIG. 8 is an IR spectrum of a phosphate salt and/or co-crystal of sepiapterin.
Figure 9:
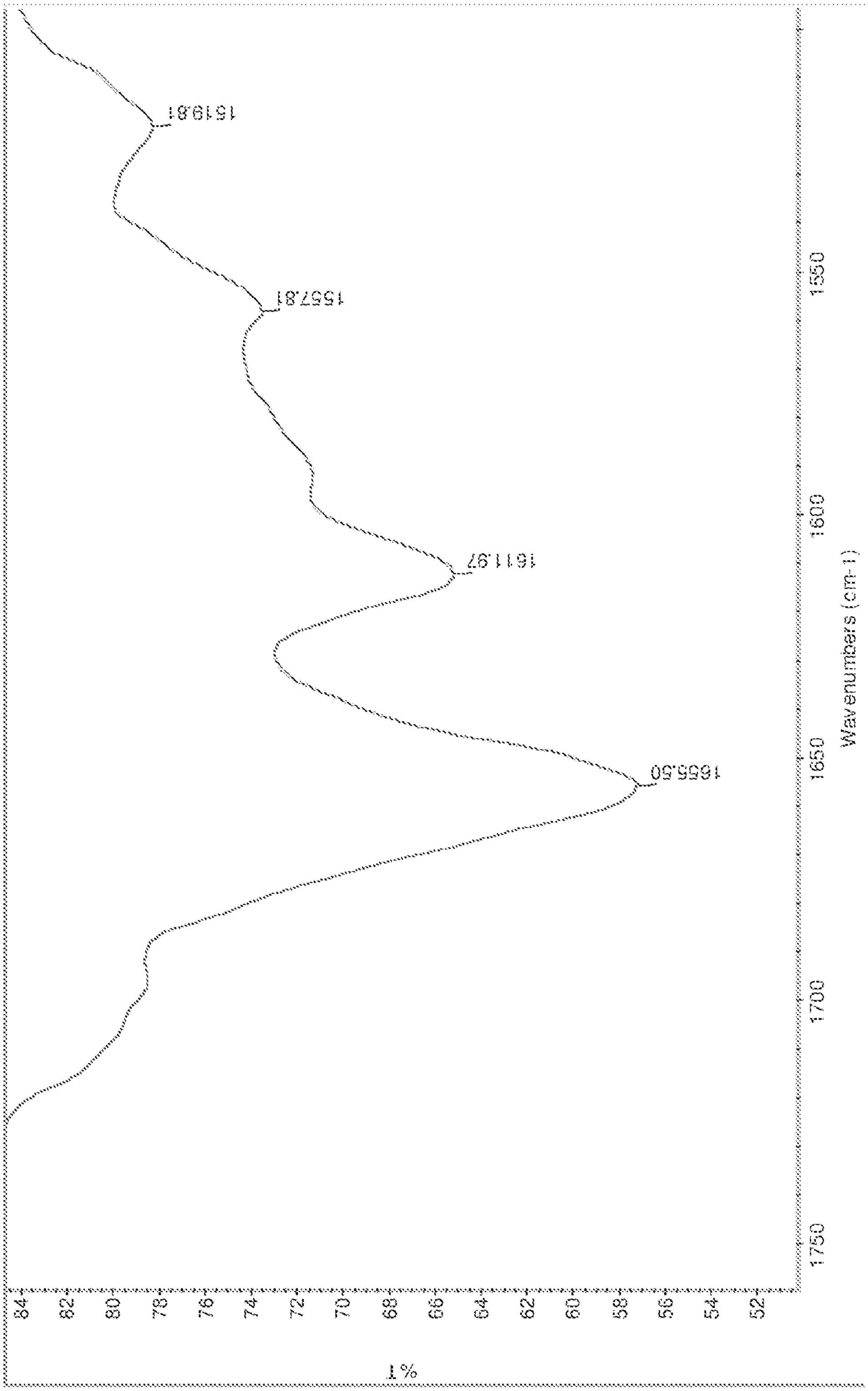
FIG. 9 is an IR spectrum of a L-tartrate salt and/or co-crystal of sepiapterin.
Figure 10:
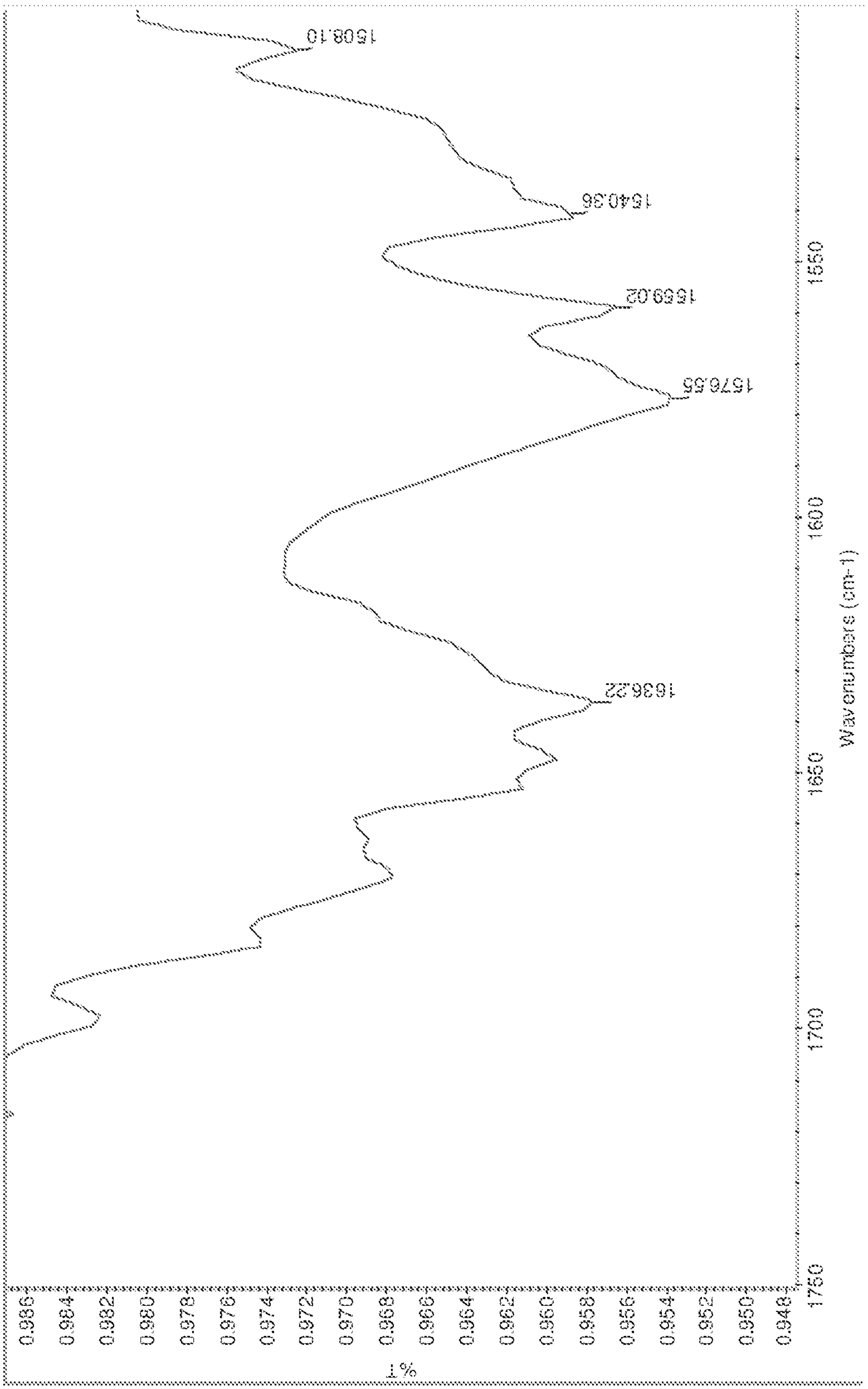
FIG. 10 is an IR spectrum of a glycolate salt and/or co-crystal of sepiapterin.
Figure 11:
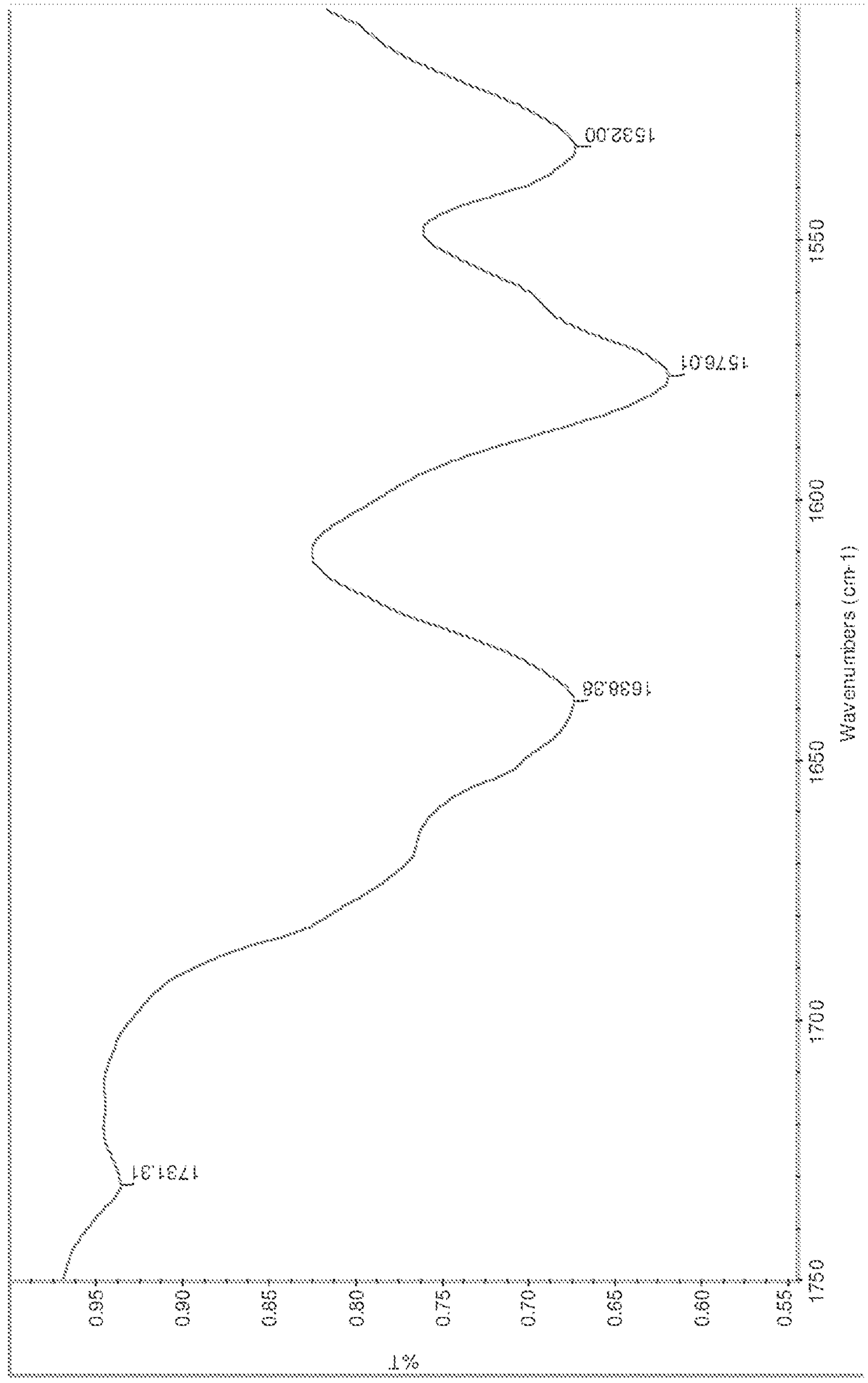
FIG. 11 is an IR spectrum of a malonate salt and/or co-crystal of sepiapterin.
Figure 12:
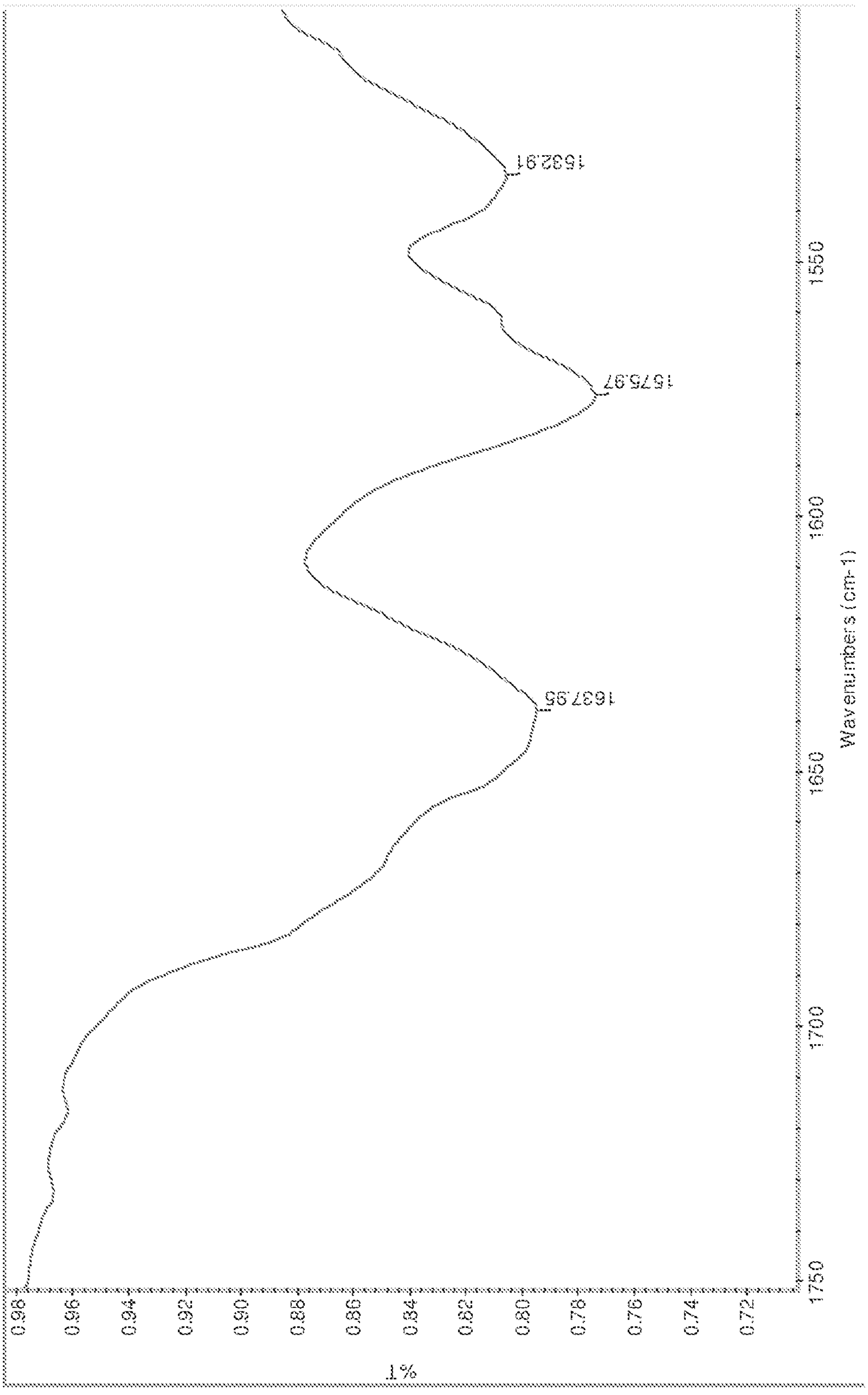
FIG. 12 is an IR spectrum of a gentisate salt and/or co-crystal of sepiapterin.
Figure 13:
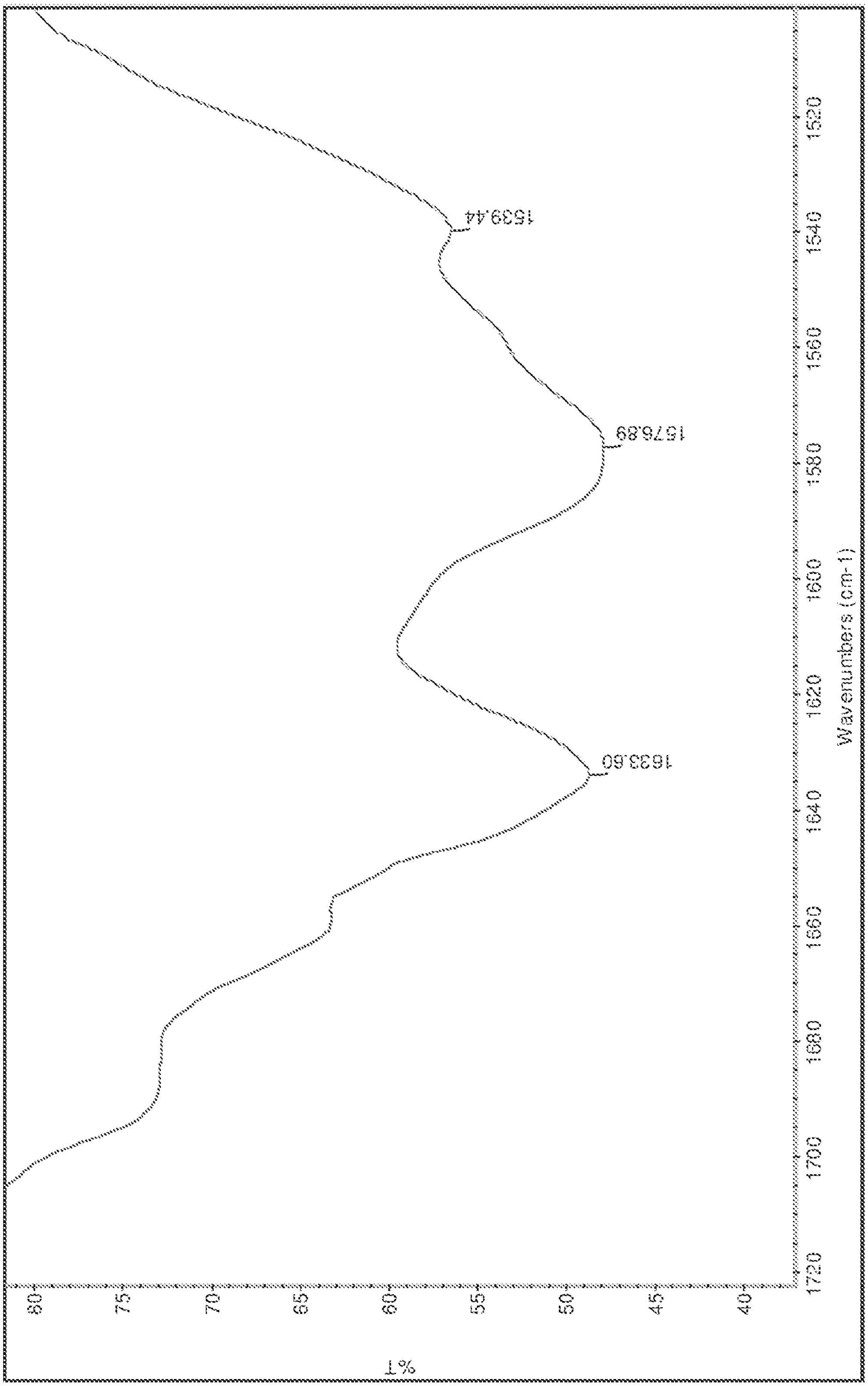
FIG. 13 is an IR spectrum of a fumarate salt and/or co-crystal of sepiapterin.

The salts were analyzed by DSC, TGA, HPLC, IR, and XRPD. The results are summarized in Table 15 below. The IR spectra are shown in FIGS. 1-13.

TABLE 15

Summary of sepiapterin salt and/or co-crystal analysis

| Salt form | Weight (mg) | TGA Weight loss (%) | DSC Endotherm (° C., onset) | Purity (%) | Molar ratio (FB: acid) | Residual solvent |
|---|---|---|---|---|---|---|
| HCI Salt | 190.9 | 3.6 | 218.3 | 93.94 | 1:1.3 | Negligible Acetone |
| Methane-sulfonate | 188.0 | 4.23 | 182.3 | 91.14 | 1:1.0 | Negligible MeOH |
| Nicotinate | 246.0 | 1.27 | 220.4 | 97.16 | 1:0.9 | None |
| Toluene-sulfonate | 256.4 | 0.5 | 190.3, 262.9 | 96.84 | 1:1.0 | None |

TABLE 15-continued

| Summary of sepiapterin salt and/or co-crystal analysis | | | | | | |
|---|---|---|---|---|---|---|
| Salt form | Weight (mg) | TGA Weight loss (%) | DSC Endotherm (° C., onset) | Purity (%) | Molar ratio (FB: acid) | Residual solvent |
| Benzene-sulfonate | 173.3 | 1.54 | 192.7, 206.2 | 90.20 | 1:1.0 | Negligible MeOH |
| Sulfate | 227.5 | 2.6 | 196.5 | 97.33 | 1:0.6 | None |
| Phosphate | 235.8 | 11.2 | 144.0, 206.8 | 96.75 | 1:1.1 | None |
| Malonate | 95.8 | 3.83 | 175.1 | 99.45 | TBD | None |
| L-Tartrate | 232.2 | 1.14 | 156.5, 174.6 | 99.75 | 1:1.0 | Negligible Acetone |
| Fumarate | 217.3 | 4.81 | 77.3, 132.8, 190.1 | 99.46 | 1:0.6 | Negligible Acetone |
| Gentisate | 98.1 | 6.92 | 83.2, 133.8, 149.0 | 94.35 | 1:0.5 | None |
| Glycolate | 135.4 | 20.15 | 79.3, 90.0, 132.3, 151.6 | 99.19 | 1:0.3 | None |

FB = free base

Example 2. Stability Analysis of Salts and/or Co-Crystals of Sepiapterin

The stability of the prepared salts and/or co-crystals was analyzed after 1 and 2 weeks at 25° C. and 60% relative humidity and 40° C. and 75% relative humidity. The results are summarized in Table 16 below. Surprisingly, of all the salts and/or co-crystals tested, the phosphate salt and/or co-crystal, the tartrate salt and/or co-crystal, and the nicotinate salt and/or co-crystal were noticeably more stable than the others. None of the phosphate, tartrate, or nicotinate salts and/or co-crystals underwent a form change during the stability testing, and each of them retained greater than 97% purity over the two weeks of the study. In fact, both the tartrate and nicotinate both retained greater than 99% purity.

TABLE 16

| Summary of stability study results | | | | | |
|---|---|---|---|---|---|
| Salt | Time point | Condition | Form change | Purity (Area %) | Purity vs. initial (%) |
| Phosphate | Initial | NA | NA | 96.75 | NA |
| | 1 week | 25° C./ 60% RH | No | 95.35 | 98.6 |
| | | 40° C./ 75% RH | No | 95.91 | 99.1 |
| | 2 weeks | 25° C./ 60% RH | No | 95.87 | 99.1 |
| | | 40° C./ 75% RH | No | 94.50 | 97.7 |
| L-Tartrate | Initial | NA | NA | 99.75 | NA |
| | 1 week | 25° C./ 60% RH | No | 98.61 | 99.9 |
| | | 40° C./ 75% RH | No | 99.06 | 99.3 |
| | 2 weeks | 25° C./ 60% RH | No | 99.39 | 99.6 |
| | | 40° C./ 75% RH | No | 99.00 | 99.3 |
| Glycolate | Initial | NA | NA | 99.19 | NA |
| | 1 week | 25° C./ 60% RH | Glycolate and free base | 98.93 | 99.7 |
| | | 40° C./ 75% RH | Glycolate and free base | 98.54 | 99.3 |
| | 2 weeks | 25° C./ 60% RH | Glycolate and free base | 98.86 | 99.7 |
| | | 40° C./ 75% RH | Glycolate and free base | 98.52 | 99.3 |

TABLE 16-continued

| Summary of stability study results | | | | | |
|---|---|---|---|---|---|
| Salt | Time point | Condition | Form change | Purity (Area %) | Purity vs. initial (%) |
| Fumarate | Initial | NA | NA | 99.46 | NA |
| | 1 week | 25° C./ 60% RH | No | 99.39 | 99.9 |
| | | 40° C./ 75% RH | No | 99.15 | 99.7 |
| | 2 weeks | 25° C./ 60% RH | Fumarate and free base | 99.25 | 99.7 |
| | | 40° C./ 75% RH | Fumarate and free base | 98.98 | 99.5 |
| Gentisate | Initial | NA | NA | 94.35 | NA |
| | 1 week | 25° C./ 60% RH | Gentisate and free base | 97.66 | 103.5 |
| | | 40° C./ 75% RH | Gentisate and free base | 96.89 | 102.7 |
| | 2 weeks | 25° C./ 60% RH | Gentisate and free base | 97.00 | 102.8 |
| | | 40° C./ 75% RH | Gentisate and free base | 93.37 | 102.1 |
| | Initial | NA | NA | 99.45 | NA |
| Malonate | 1 week | 25° C./ 60% RH | Malonate and free base | 99.39 | 99.9 |
| | | 40° C./ 75% RH | Malonate and free base | 99.14 | 99.7 |
| | 2 weeks | 25° C./ 60% RH | Malonate and free base | 99.23 | 99.8 |
| | | 40° C./ 75% RH | Malonate and free base | 97.81 | 98.3 |
| HCI | Initial | NA | NA | 93.94 | NA |
| | 1 week | 25° C./ 60% RH | No | 97.19 | 103.5 |
| | | 40° C./ 75% RH | No | 89.25 | 95.0 |
| | 2 weeks | 25° C./ 60% RH | No | 91.84 | 97.8 |
| | | 40° C./ 75% RH | No | 84.16 | 89.6 |
| Methane-sulfonate | Initial | NA | NA | 91.14 | NA |
| | 1 week | 25° C./ 60% RH | No | 95.26 | 104.5 |
| | | 40° C./ 75% RH | No | 88.68 | 97.3 |
| | 2 weeks | 25° C./ 60% RH | No | 91.95 | 100.9 |
| | | 40° C./ 75% RH | No | 85.97 | 94.3 |
| Nicotinate | Initial | NA | NA | 97.16 | NA |
| | 1 week | 25° C./ 60% RH | No | 97.43 | 100.3 |
| | | 40° C./ 75% RH | No | 97.30 | 100.2 |
| | 2 weeks | 25° C./ 60% RH | No | 97.45 | 100.3 |
| | | 40° C./ 75% RH | No | 97.41 | 100.3 |
| Toluene-sulfonate | Initial | NA | NA | 96.84 | NA |
| | 1 week | 25° C./ 60% RH | No | 94.19 | 97.3 |
| | | 40° C./ 75% RH | No | 89.11 | 92.0 |
| | 2 weeks | 25° C./ 60% RH | No | 91.40 | 94.4 |
| | | 40° C./ 75% RH | No | 88.12 | 91.0 |
| Benzene-sulfonate | Initial | NA | NA | 90.20 | NA |
| | 1 week | 25° C./ 60% RH | No | 90.68 | 100.5 |
| | | 40° C./ 75% RH | No | 82.63 | 91.6 |
| | 2 weeks | 25° C./ 60% RH | No | 86.37 | 95.8 |
| | | 40° C./ 75% RH | No | 82.65 | 91.6 |

TABLE 16-continued

Summary of stability study results

| Salt | Time point | Condition | Form change | Purity (Area %) | Purity vs. initial (%) |
|---|---|---|---|---|---|
| Sulfate | Initial | NA | NA | 97.33 | NA |
| | 1 week | 25° C./ 60% RH | No | 95.22 | 97.8 |
| | | 40° C./ 75% RH | No | 89.44 | 91.9 |
| | 2 weeks | 25° C./ 60% RH | No | 93.46 | 96.0 |
| | | 40° C./ 75% RH | No | 88.20 | 90.6 |

NA = Not applicable;
RH = relative humidity

Example 3. Solubility and Disproportionation of Various Sepiapterin Salts and/or Co-Crystals The kinetic solubility was evaluated for nicotinate, phosphate, L-tartrate, and fumarate salts and/or co-crystals of sepiapterin in water and Medisca Oral Mix. X-ray powder diffraction (XRPD) was performed for the residual solids to identify form change/disproportionation. Solids were suspended into the media with target conc. of 7 mg/mL (calculated by freebase). The suspensions were agitated on a rolling incubator at 25 rpm for 1, 4 and 24 hrs. At each time point, 1 mL of the suspension was pipetted out for centrifugation at 10000 rpm (2 min) and filtration through 0.45 μm membrane to obtain supernatant for HPLC solubility and pH tests, the residual solids were analyzed by XRPD. The solubility results are summarized in Tables 17-20.

TABLE 17

Solubility summary of nicotinate salt and/or co-crystal

| Media | Time point (hr) | Temp. (° C.) | Solubility (mg/mL)* | Purity (area %)# | Observation | Form change | PH |
|---|---|---|---|---|---|---|---|
| Water | 1 | RT | 1.5 | 98.97 | Turbid | Yes | 2.1 |
| | 4 | | 2.3 | 99.04 | Turbid | Yes | 2.1 |
| | 24 | | 1.8 | 96.54 | Turbid | Yes | 2.1 |
| Medisca | 1 | | 2.6 | 99.76 | Turbid | Yes | 3.1 |
| Oral | 4 | | 3.1 | 99.60 | Turbid | Yes | 3.1 |
| Mix | 24 | | 3.5 | 97.00 | Turbid | Yes | 3.1 |

*Calculated using freebase.
#Excess amount of salt sample was dosed for solubility measurement, which may lead to impurity enrichment in supernatant, so the purity data is for reference only.

TABLE 18

Solubility summary of phosphate salt and/or co-crystal

| Media | Time point (hr) | Temp. (° C.) | Solubility (mg/mL)* | Purity (area %)# | Observation | Form change | PH |
|---|---|---|---|---|---|---|---|
| Water | 1 | RT | 1.7 | 89.92 | Turbid | Yes | 2.1 |
| | 4 | | 2.0 | 89.52 | Turbid | Yes | 2.1 |
| | 24 | | 1.9 | 82.64 | Turbid | Yes | 2.1 |
| Medisca | 1 | | 2.5 | 99.23 | Turbid | Yes** | 3.1 |
| Oral | 4 | | 3.2 | 98.95 | Turbid | Yes** | 3.1 |
| Mix | 24 | | 2.1 | 87.63 | Turbid | Yes** | 3.1 |

*Calculated using freebase.
**Low crystallinity.
#Excess amount of salt sample was dosed for solubility measurement, which may lead to impurity enrichment in supernatant, so the purity data is for reference only.

TABLE 19

Solubility summary of L-tartrate salt and/or co-crystal

| Media | Time point (hr) | Temp. (° C.) | Solubility (mg/mL)* | Purity (area %)# | Observation | Form change | PH |
|---|---|---|---|---|---|---|---|
| Water | 1 | RT | 1.6 | 99.34 | Turbid | Yes | 2.5 |
| | 4 | | 1.8 | 99.07 | Turbid | Yes | 2.5 |
| | 24 | | 1.8 | 95.61 | Turbid | Yes | 2.5 |
| Medisca | 1 | | 2.0 | 99.68 | Turbid | Yes | 3.3 |
| Oral | 4 | | 2.5 | 99.54 | Turbid | Yes | 3.3 |
| Mix | 24 | | 3.2 | 95.67 | Turbid | Yes | 3.3 |

*Calculated using freebase.
#Excess amount of salt sample was dosed for solubility measurement, which may lead to impurity enrichment in supernatant, so the purity data was for reference only.

TABLE 20

Solubility summary of fumarate salt and/or co-crystal

| Media | Time point (hr) | Temp. (° C.) | Solubility (mg/mL)* | Purity (area %)# | Observation | Form change | PH |
|---|---|---|---|---|---|---|---|
| Water | 1 | RT | 1.2 | 98.39 | Turbid | No | 3.1 |
| | 4 | | 1.4 | 98.19 | Turbid | No | 3.1 |
| | 24 | | 1.5 | 95.43 | Turbid | No | 3.1 |
| Medisca | 1 | | 2.2 | 99.74 | Turbid | No ** | 4.0 |
| Oral | 4 | | 3.1 | 99.60 | Turbid | No ** | 4.0 |
| Mix | 24 | | 2.9 | 96.54 | Turbid | No ** | 4.0 |

*Calculated using freebase.
**Low crystallinity
#Excess amount of salt sample was dosed for solubility measurement, which may lead to impurity enrichment in supernatant, so the purity data was for reference only.

Results: For the nicotinate, phosphate, and L-tartrate salts and/or co-crystals, the residual solids converted to freebase in water and Medisca Oral Mix after 1 hour. For the fumarate salt and/or co-crystal, no form change was observed for the residual solids in water while the crystallinity of residual solids decreased after 1 hour in Medisca Oral Mix. Surprisingly, of the twelve different salt and/or co-crystal forms studied, the fumarate salt and/or co-crystal was the only salt and/or co-crystal found to have high stability in the solid form stability study of Example 2 and show no evidence of disproportionation in the disproportionation study.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

What is claimed:

1. A pharmaceutically acceptable salt of sepiapterin, wherein the pharmaceutically acceptable salt is a nicotinate salt, a 1:1 tartrate salt, or a 2:1 tartrate salt.

2. The pharmaceutically acceptable salt of claim 1, wherein the pharmaceutically acceptable salt is a nicotinate salt.

3. The pharmaceutically acceptable salt of claim 1, wherein the pharmaceutically acceptable salt is a 1:1 tartrate salt or a 2:1 tartrate salt.

4. The pharmaceutically acceptable salt of claim 3, wherein the pharmaceutically acceptable salt is a 1:1 tartrate salt.

5. The pharmaceutically acceptable salt of claim 3, wherein the pharmaceutically acceptable salt is a 2:1 tartrate salt.

6. The pharmaceutically acceptable salt of claim 1 wherein the salt is crystalline.

7. The pharmaceutically acceptable salt of claim 6 comprising less than 40% by weight of amorphous compound.

8. A pharmaceutical composition comprising the pharmaceutically acceptable salt of claim 1 and a pharmaceutically acceptable excipient.

* * * * *